United States Patent
Harris, Sr. et al.

(10) Patent No.: US 10,262,383 B1
(45) Date of Patent: Apr. 16, 2019

(54) SYSTEMS AND METHODS FOR DETERMINING OPERATIONAL STATUS OF THIRD-PARTY SERVICE PROVIDERS

(71) Applicant: MCKESSON CORPORATION, San Francisco, CA (US)

(72) Inventors: Patrick I. Harris, Sr., Brookhaven, GA (US); Roger G. Pinsonneault, Alpharetta, GA (US)

(73) Assignee: MCKESSON CORPORATION, San Francisco, CA (US)

( * ) Notice: Subject to any disclaimer, the term of this patent is extended or adjusted under 35 U.S.C. 154(b) by 1077 days.

(21) Appl. No.: 14/639,532

(22) Filed: Mar. 5, 2015

(51) Int. Cl.
*G06Q 20/02* (2012.01)
*G06Q 50/22* (2018.01)

(52) U.S. Cl.
CPC ........... *G06Q 50/22* (2013.01); *G06Q 20/027* (2013.01)

(58) Field of Classification Search
CPC .............................. G06Q 20/027; G06Q 50/22
USPC .......................................................... 705/2–3
See application file for complete search history.

(56) References Cited

U.S. PATENT DOCUMENTS

| | | | |
|---|---|---|---|
| 5,892,818 A * | 4/1999 | Lee ....................... | H04M 3/365 379/112.04 |
| 6,456,624 B1 | 9/2002 | Eccles et al. | |
| 7,114,158 B1 | 9/2006 | Thompson et al. | |
| 7,489,628 B2 | 2/2009 | Pirbhai et al. | |
| 8,327,020 B1 * | 12/2012 | Sarathi ................... | G06Q 50/22 709/239 |
| 8,429,448 B1 | 4/2013 | Vohra et al. | |
| 8,522,241 B1 | 8/2013 | Vohra et al. | |
| 8,639,531 B2 * | 1/2014 | Hasan .................... | G06Q 10/00 705/3 |
| 2002/0035606 A1 | 3/2002 | Kenton | |
| 2003/0009560 A1 | 1/2003 | Venkitaraman | |
| 2004/0199926 A1 | 10/2004 | Gilgen et al. | |
| 2005/0188107 A1 | 8/2005 | Piercey et al. | |
| 2005/0249497 A1 | 11/2005 | Haran et al. | |

(Continued)

OTHER PUBLICATIONS

Matt Welsh; SEDA: An Architecture for WellConditions, Scalabe Internet Services; ACM 2001; 20 pages.

(Continued)

*Primary Examiner* — Joy Chng
(74) *Attorney, Agent, or Firm* — Alston & Bird LLP

(57) ABSTRACT

Systems and methods are provided for determining the operational status of third-party switch/service providers. The service provider computer receives healthcare transactions and determines if each transaction is to be processed by a third-party switch provider system, either under a contract between the pharmacy and the third-party switch provider or under an exclusivity arrangement between the transaction payer and the third-party switch provider. Healthcare transactions are sent to the third-party switch provider for processing. If the transmission is not successful, the service provider computer will determine if the third-party switch provider system is operating. If determined to not be operating, the service provider computer will process on its own the healthcare transactions that are typically processed by the third-party switch provider system due to contractual agreement with the pharmacy that sent the transaction for as long as the third-party switch provider system is determined to be not operating.

20 Claims, 6 Drawing Sheets

(56) References Cited

U.S. PATENT DOCUMENTS

2005/0288964 A1* 12/2005 Lutzen .................. G06F 19/328
                                                        705/2
2011/0040810 A1   2/2011  Kaplan et al.
2011/0247003 A1  10/2011  Fong et al.
2012/0060062 A1   3/2012  Lin et al.
2012/0060165 A1   3/2012  Clarke

OTHER PUBLICATIONS

Matt Welsh; The Staged Event-Driven Architecture for Highly-Concurrent Server Applications; Qualifying Examination Proposal, Nov. 2000; 26 pages.
Non-Final Office Action for U.S. Appl. No. 12/893,546 dated Aug. 1, 2012.
Notice of Allowance for U.S. Appl. No. 12/893,546 dated Oct. 11, 2012.
Non-Final Office Action for U.S. Appl. No. 12/893,693 dated Feb. 6, 2013.
Notice of Allowance for U.S. Appl. No. 12/965,511 dated Feb. 26, 2013.
Notice of Allowance for U.S. Appl. No. 12/893,693 dated Apr. 30, 2013.

* cited by examiner

SYSTEMS AND METHODS FOR DETERMINING OPERATIONAL STATUS OF THIRD-PARTY SERVICE PROVIDERS

TECHNICAL FIELD

Aspects of the disclosure relate generally to the electronic transmission of healthcare transactions, and more particularly, to systems and methods for determining operational status of third-party switch provider systems for receipt and processing of electronically submitted healthcare transactions.

BACKGROUND

In the healthcare industry, there are multiple service providers or switch providers that act as intermediaries between pharmacies and healthcare transaction claims processors (e.g., pharmacy benefits manager (PBM), an insurer, a Medicare payer, Medicaid payer, accountable care organization, other governmental healthcare insurance payer, or other third-party payer), medication and/or medical product manufacturers, coupon vendors, and the like. These service/switch provider systems can receive healthcare transactions from the pharmacy, via a pharmacy computer, and can pass along the healthcare transaction to the proper claims processor, manufacturer, coupon vendor, etc., via the claims processor computer, for adjudication or other processing. These service/switch provider systems may also provide many services to the pharmacies, claims processors, or manufacturers based on the healthcare transactions that are processed by the particular service/switch provider systems.

In certain situations, one switch/service provider computer may receive a healthcare transaction and may need to transmit it to another switch/service provider computer that is wholly unrelated to the first switch/service provider computer. The exchange of transactions between unrelated switch/service provider computing systems is needed to support the delivery of financial and/or clinical healthcare transactions to payers/claims processor that have an exclusive agreement with one of the switch/service provider systems. For example if a Claims processor A has an exclusive arrangement with Service provider B for the processing of healthcare transactions, but the healthcare transaction is originally transmitted to Service provider A and the healthcare transaction identifies claims processor A as the intended payer destination, Service provider A would transmit the healthcare transaction that is intended for claims processor A to Service provider B. This is done because Service provider A is not authorized to process transactions that are intended for claims processor A.

The exchange of transactions between unrelated switch/service provider computing systems is needed to support the delivery of financial and/or clinical healthcare transactions to hub service business models in which a participating pharmacy wants to access value added services provided by Service provider B but sends its healthcare transactions initially to Service provider A. An example of this situation is when a pharmacy practice management system software vendor or pharmacy chain contracts with Service provider A for hub/switch services and requests sharing of their healthcare transactions with Service Provider B for value-added services.

A problem results in this scenario when Service provider B experiences a network outage or degradation in performance (e.g., the Service provider B computing system is not operating). When this occurs, a participating pharmacy is unable to deliver their financial and/or clinical healthcare transactions to their intended recipients (i.e. claims processors, manufacturers and/or coupon vendors). Without the ability to have its healthcare transactions adjudicated, the pharmacy is not able to provide prescription dispensing services to its customers. This can lead to lost customers or the customers having to come back at a later time when the Service provider B system is hopefully back to an operational state.

BRIEF DESCRIPTION OF THE DRAWINGS

Reference will now be made to the accompanying drawings, which are not necessarily drawn to scale, and wherein.

DETAILED DESCRIPTION OF EXAMPLE EMBODIMENTS

Exemplary embodiments will now be described more fully hereinafter with reference to the accompanying drawings, in which exemplary embodiments are shown. The concepts disclosed herein may, however, be embodied in many different forms and should not be construed as limited to the exemplary embodiments set forth herein; rather, these embodiments are provided so that this disclosure will be thorough and complete, and will fully convey the scope of the concepts to those skilled in the art. Like numbers refer to like, but not necessarily the same or identical, elements throughout.

System Overview

Figure 1:
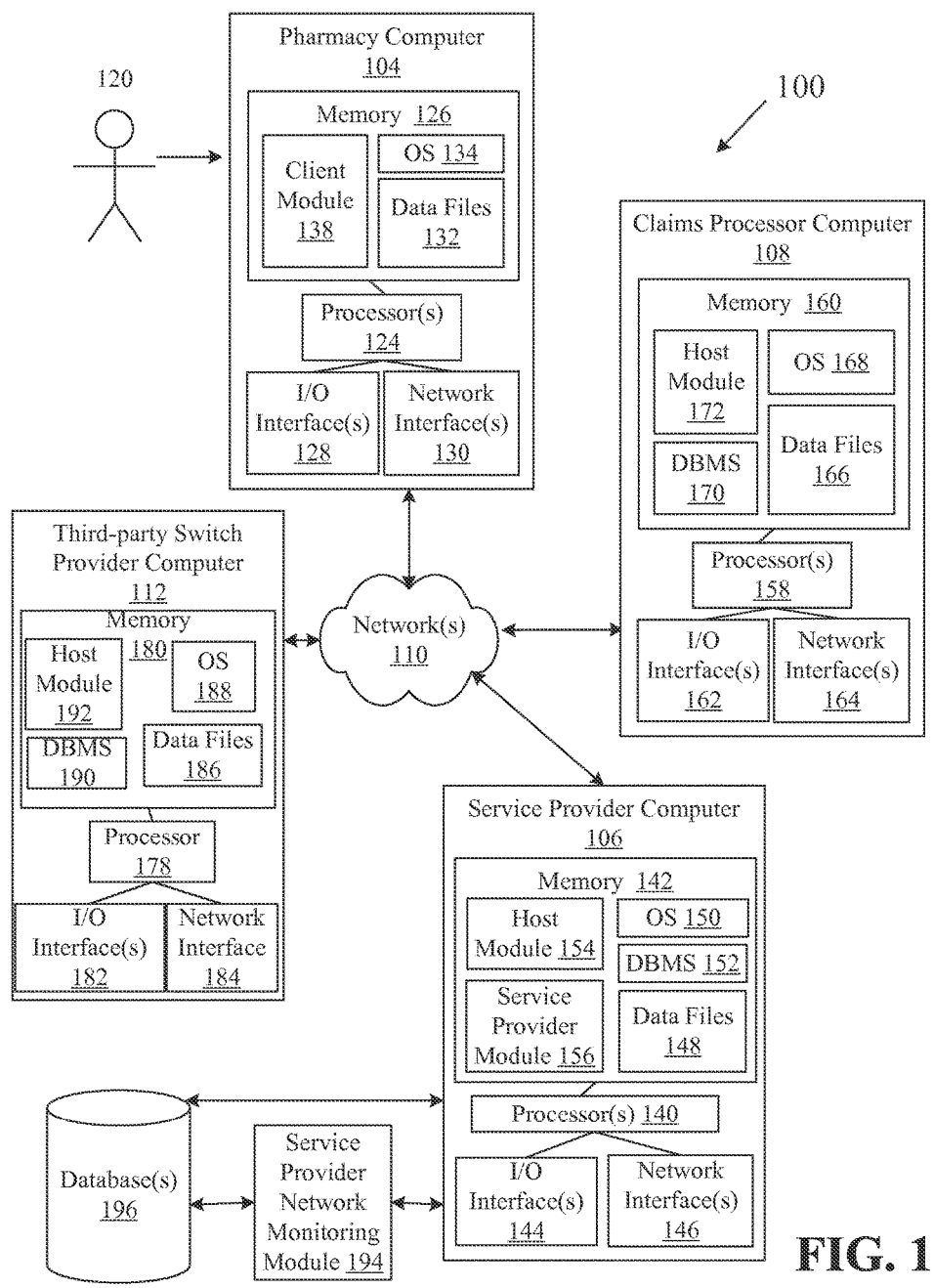
FIG. 1 illustrates an example overview of a system that facilitates a determination of the operational status of third-party switch provider systems for receipt and processing of electronically submitted healthcare transactions from another intermediary, such as a service provider computer, according to one exemplary embodiment of the disclosure.

FIG. 1 illustrates an example system 100 supporting healthcare transactions, electronic prescription ordering activities, prescription billing activities, and patient coverage eligibility verifications according to one example embodiment. The exemplary system 100 facilitates a determination of the operational status of one or more third-party switch provider systems for receipt and processing of electronically submitted healthcare transactions, including, but not limited to, an eligibility verification request, predetermination of benefits transaction, prescription claim transaction, prescription claim or billing request, healthcare order transaction, or e-prescription transaction (e.g., electronic prescription order transaction, e-script, or e-prescription) from another intermediary, such as a service provider computer 106, and will now be described illustratively with respect to FIG. 1. As described herein, the service provider computer 106 and associated service provider are separate, distinct, and wholly-unrelated entities from the third-party switch provider computer 112 and associated third-party switch provider. As shown in FIG. 1, the system 100 may include one or more pharmacy computers 104, at least one service provider computer 106, one or more third-party switch provider computers 112, at least one service provider network monitoring module 194 and one or more claims processor computers 108.

As desired, each of the pharmacy computers 104, service provider computer 106, service provider network monitoring module 194, third-party switch provider computers 112, and/or claims processor computers 108 may include one or more processing devices that may be configured for accessing and reading associated computer-readable media having stored thereon data and/or computer-executable instructions for implementing the various methods disclosed in the exemplary embodiments discussed herein.

Additionally, in certain exemplary embodiments, the service provider computer 106 and/or the service provider network monitoring module 194 may be in communication with one or more data storage devices, such as database 196. The database 196 may receive, store, and provide, as needed, healthcare transactions data and network status data for the third-party switch computers 112 from the service provider computer 106 and/or the service provider network monitoring module 194. In certain exemplary embodiments, the healthcare transactions data includes all or any portion of the data included in healthcare transactions received by the service provider computer 106 from one or more pharmacy computers 104 and/or adjudicated responses to healthcare transactions from one or more claims processor computers 108. In addition, the database 196 or another database may include a table, schedule, or listing correlating payer identifiers to one of i) exclusively receiving healthcare transactions from the third-party switch provider computer; ii) exclusively receiving healthcare transactions from the service provider computer; and iii) can receive healthcare transactions from both the service provider computer and the third-party switch provider computer. Further the database 196 or another database may include a table, schedule, or listing correlating pharmacy identifiers to the intermediary the each pharmacy has contracted with (either the service provider computer 106 or one of the third-party switch computers 112) to receive healthcare transactions from the respective pharmacy and to pass those healthcare transactions along the to the identified claims processor computer 108. Further, the database 196 or another database may include threshold limits (e.g., time threshold for time-outs to the third-party switch provider computer 112, one or more thresholds for percentage and/or number of transactions timed-out, non-responsive, or rejected by the third-party switch provider computer 112 for determining that the third-party switch provider computer 112 is not currently operating properly and needs to be bypassed, and corresponding thresholds for determining when the third-party switch provider computer 112 is once-again operating properly), and counters for determining the number and/or percentage of times a transmission from the service provider computer 106 to the third-party switch provider computer 112 fails or is successful. Alternatively, the data storage function may be included in the service provider computer 106 and/or the service provider network monitoring module 194 itself, such as in the memory 142 of the service provider computer 106.

Generally, network devices and systems, including one or more of the pharmacy computers 104, service provider computer 106, service provider network monitoring module 194, third-party switch provider computers 112 and claims processor computers 108 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the one or more pharmacy computers 104, service provider computer 106, claims processor computers 108, service provider network monitoring module 194, third-party switch provider computers 112, and database 196 may be in communication with each other via one or more networks, such as network 110, which as described below can include one or more separate or shared private and public networks, including the Internet or a publicly switched telephone network. Each of these components, the one or more pharmacy computers 104, service provider computer 106, claims processor computers 108, service provider network monitoring module 194, third-party switch provider computers 112, database 196, and the network 110 will now be discussed in further detail.

Each pharmacy computer 104 may be associated with (e.g., located within and/or providing computing services for) a pharmacy. Each pharmacy computer 104 may be any suitable processor-driven device that facilitates the processing of healthcare requests made by patients or consumers and the communication of information associated with healthcare transactions to the service provider computer 106, such as a server computer, a mainframe computer, one or more networked computers, a desktop computer, a personal computer, a digital assistant, a personal digital assistant, a digital tablet, an Internet appliance, an application-specific circuit, microcontroller, minicomputer, or any other processor-based device. In certain embodiments, each pharmacy computer 104 may be a suitable point-of-sale device located within a pharmacy. The execution of the computer-implemented instructions by each pharmacy computer 104 may form a special purpose computer or other particular machine that is operable to facilitate the processing of healthcare requests made by patients and the communication of information associated with healthcare transactions to a service provider computer 106. Additionally, in certain example embodiments, the operations and/or control of each pharmacy computer 104 may be distributed amongst several processing components.

In addition to having one or more processors 124, each healthcare provider computer 104 may include one or more memory devices 126, one or more input/output ("I/O") interfaces 128, and one or more network interfaces 130. The memory devices 126 may be any suitable memory device, for example, caches, read-only memory devices, random access memory devices, magnetic storage devices, removable storage devices, etc. The memory devices 126 may store data, executable instructions, and/or various program modules utilized by the pharmacy computer 104, for example, data files 132, an operating system ("OS") 134, and/or a client module 138, respectively. The data files 132 may include any suitable data that facilitates the receipt and/or processing of healthcare requests by the pharmacy computer 104 and the generation and/or processing of healthcare transactions that are communicated to the service provider computer 106. For example, the data files 132 may include, but are not limited to, healthcare information and/or contact information associated with one or more patients, information associated with the particular pharmacy and/or the respective pharmacy computer 104, information associated with the service provider computer 106, information associated with one or more claims processors and/or claims processor computers 108, and/or information associated with one or more healthcare transactions. The OS 134 may be any suitable software module that controls the general operation of the pharmacy computer 104. The OS 134 may also facilitate the execution of other software modules by the one or more processors 124, for example, the client module 138. The OS 134 may be any currently existing or future-developed operating system including, but not limited to, Microsoft Windows®, Apple OSX™, Linux, Unix, or a mainframe operating system.

The client module 138 may be an Internet browser or other suitable software, including a dedicated program, for interacting with the service provider computer 106. For example, a user 120 such as a pharmacist, pharmacy assistant, nurse practitioner, physician, nurse, or other pharmacy, hospital, physician's office, or other healthcare provider employee may utilize the client module 138 in preparing and transmitting a healthcare transaction, such as a predetermination of benefits transaction, healthcare claim transaction, prescription claim or billing request, healthcare order transaction, or e-prescription transaction (e.g., electronic prescription order transaction, e-script, or e-prescription), to the service provider computer 106 for delivery to the either the appropriate other intermediary (e.g., third-party switch provider computer 112) the appropriate claims processor computer 108 or other third-party for adjudication or other coverage/benefits determination. The pharmacy computer 104 may also utilize the client module 138 to retrieve or otherwise receive data, messages, or responses from the service provider computer 106 and/or other components of the system 100. For example, in certain example embodiments, the client module 138 may be utilized to receive a rejection of the healthcare transaction and/or an adjudicated healthcare transaction from the service provider computer 106 as will be described below.

The one or more I/O interfaces 128 may facilitate communication between the pharmacy computer 104 and one or more input/output devices, for example, one or more user interface devices, such as, a display, keypad, keyboard, control panel, touch screen display, remote control, mouse, microphone, etc. that facilitate user interaction with the pharmacy computer 104. For example, the one or more I/O interfaces 128 may facilitate entry of information included in a healthcare transaction by an employee 120 of a pharmacy, such as a pharmacy employee, pharmacist, physician, nurse, hospital employee, or nurse practitioner affiliated with a pharmacy, hospital, physician's office or other similar healthcare provider. The one or more network interfaces 130 may facilitate connection of the pharmacy computer 104 to one or more suitable networks, for example, the network 110 illustrated in FIG. 1. In this regard, each pharmacy computer 104 may receive and/or communicate information to other network components of the system 100, such as the service provider computer 106.

With continued reference to FIG. 1, the service provider computer 106 may include, but is not limited to, any suitable processor-driven device that is configured for receiving, processing, and fulfilling requests from the one or more pharmacy computers 104, one or more third-party switch provider computers 112, the service provider network monitoring module 194, the one or more databases 196, and/or the one or more claims processor computers 108 relating to pharmacy, benefits, billing, electronic prescription submission, and/or other healthcare transactions and/or other activities. In certain exemplary embodiments, the service provider computer 106 may be a switch/router computer or intermediary that routes healthcare transactions and/or other healthcare requests from a pharmacy computer to a claims processor computer or third-party switch provider computer 112. For example, the service provider computer 106 may route healthcare claim transactions communicated from the pharmacy computer 104 (at e.g., a pharmacy) to a claims processor computer 108, such as a pharmacy benefits manager (PBM), an insurer, a Medicare payer, Medicaid payer, other governmental healthcare insurance payer, or other third-party payer. In another example, the service provider computer 106 may receive a healthcare claim transaction from the pharmacy computer 104, determine the payer identifier identifies a payer that is exclusively serviced by one of the third-party switch provider computers 112 as the switch/router, and can route the healthcare claim transaction to the proper third-party switch provider computer 112.

In certain embodiments, the service provider computer 106 may include a suitable host server, host module, or other software that facilitates the receipt of a healthcare transaction from a pharmacy computer 104 and/or the routing of the received healthcare transaction to a claims processor computer 108 or third-party switch provider computer 112. Any number of pharmacy computers 104, third-party switch provider computers 112, service provider network monitoring modules 194, databases 196, and/or claims processor computers 108 may be in communication with the service provider computer 106, via the network 110 for example, as desired in various embodiments.

The service provider computer 106 may include any number of special purpose computers or other particular machines, application-specific circuits, microcontrollers, personal computers, minicomputers, mainframe computers, servers, networked computers, and/or other processor-driven devices. In certain embodiments, the operations of the service provider computer 106 may be controlled by computer-executed or computer-implemented instructions that are executed by one or more processors 140 associated with the service provider computer 106 to form a special purpose computer or other particular machine that is operable to facilitate the receipt, routing, and/or processing of healthcare transactions. The one or more processors 140 that control the operations of the service provider computer 106 may be incorporated into the service provider computer 106 and/or in communication with the service provider computer 106 via one or more suitable networks. In certain exemplary embodiments, the operations and/or control of the service provider computer 106 may be distributed amongst several processing components.

Similar to the pharmacy computer 104 described above, the service provider computer 106 may include one or more processors 140, one or more memory devices 142, one or more input/output ("I/O") interfaces 144, and one or more network interfaces 146. The one or more memory devices 142 may be any suitable memory devices, for example, caches, read only memory devices, random access memory devices, magnetic storage devices, removable memory devices, etc. The one or more memory devices 142 may store data, executable instructions, and/or various program modules utilized by the service provider computer 106, for example, data files 148, an operating system ("OS") 150, the host module 154, a service provider module 156, and a database management system ("DBMS") 152 to facilitate management of data files 148 and other data stored in the memory devices 142. The OS 150 may be a suitable software module that controls the general operation of the service provider computer 106 and/or that facilitates the execution of other software modules. The OS 150 may be any currently existing or future-developed operating system including, but is not limited to, Microsoft Windows®, Apple OSX™, Linux, Unix, or a mainframe operating system.

The service provider module 156 may be operable to perform one or more pre-edits or pre-analysis on a received healthcare transaction prior to routing or otherwise communicating the received healthcare transaction, such as a healthcare claim transaction, to a suitable claims processor computer 108 or third-party switch provider computer 112. Additionally, the service provider module 156 may be operable to perform one or more post-edits on an adjudicated reply or response that is received from a claims processor computer 108 for a healthcare transaction prior to routing the adjudicated response to one of the pharmacy computers 104. In certain example embodiments, the service provider module 156 may also be operable to perform the functions described with references to the service provider network monitoring module 194 herein. A wide variety of different pre-edits and/or post-edits may be performed by the service provider module 156 as desired in various embodiments of the disclosure.

According to one exemplary embodiment, the data files 148 may store healthcare transaction records associated with communications received from various pharmacy computers 104, various third-party switch provider computers 112, and/or various claims processor computers 108. The data files 148 may also store any number of suitable routing tables that facilitate determining the destination of communications received from a pharmacy computer 104, third-party switch provider computer 112, or claims processor computer 108. In certain example embodiments, the data discussed herein that is included in the database 196 may alternatively be stored and accessed from the data files 148. The exemplary data files 148 may also store records containing, for example, patient identification data, healthcare transactions, and tables identifying pharmacies and claims processors associated with the claims processor computers 108.

The host module 154 may receive, process, and respond to requests from the client module 138 of the pharmacy computer 104, may receive, process, and respond to requests of the service provider network monitoring module 194, may receive, process and respond to information from the host modules 192 of the third-party switch provider computers 112 and/or regarding the third-party switch provider computers 112, and may further receive, process, and respond to requests of the host module 172 of the claims processor computer 108. The service provider computer 106 may include additional program modules for performing other processing methods described herein. Those of ordinary skill in the art will appreciate that the service provider computer 106 may include alternate and/or additional components, hardware or software without departing from exemplary embodiments of the disclosure.

With continued reference to the service provider computer 106, the one or more I/O interfaces 144 may facilitate communication between the service provider computer 106 and one or more input/output devices, for example, one or more user interface devices, such as a display, keypad, keyboard, mouse, control panel, touch screen display, remote control, microphone, etc. that facilitate user interaction with the service provider computer 106. The one or more network interfaces 146 may facilitate connection of the service provider computer 106 to one or more suitable networks, for example, the network 110 illustrated in FIG. 1. In this regard, the service provider computer 106 may communicate with other components of the system 100.

One or more service provider network monitoring modules 194 may also be operative with or included with or in the service provider computer 106. The service provider network monitoring module 180 may include computer-executable instructions for facilitating healthcare transaction evaluation to determine if the healthcare transaction is one for which the service provider 106 acts as the intermediary switch or if another third-party switch computer 112 acts as the intermediary switch for that particular healthcare transaction. In addition, the service provider network monitoring module 194 can monitor the healthcare transactions sent to the third-party switch provider computer 112 and can determine if those healthcare transactions are received and processed by the third-party switch provider computer 112 or alternately if the transmission of the healthcare transaction by the service provider computer 106 times-out, is rejected, or is not responded to by the third-party switch provider computer 112. Further, the service provider network monitoring module 112 can maintain a tally, count, or percentage of those healthcare transactions sent over a predetermined period of time to the third-party switch provider computer 112 by the service provider computer 106 that time-out, are rejected and/or which receive no response and can determine if the third-party switch provider computer is operating properly (e.g., the system 112 is up) or not (e.g., the system 112 is down).

In one example embodiment, the service provider network monitoring module 194 may be implemented as computer-implemented instructions of the memory 128 of the service provider computer 104. Alternatively, the service provider network monitoring module 194 may also be implemented as computer-implemented instructions of a memory of a separate processor-based system, according to another example embodiment.

Each third-party switch provider computer 112 of FIG. 1 may include a processor-driven device that is configured for receiving, processing, and fulfilling requests from the one or more pharmacy computers 104, the service provider computer 106, and/or the one or more claims processor computers 108 relating to pharmacy, benefits, billing, electronic prescription submission, and/or other healthcare transactions and/or other activities. In certain exemplary embodiments, the third-party switch provider computer 112 may be a switch/router computer or intermediary that routes healthcare transactions and/or other healthcare requests from a pharmacy computer 104 to a claims processor computer 108 or from the service provider computer 106 to a claims processor computer 108. The service provider computer 106 and each of the third-party switch provider computers 112 are distinct service provider computers from one another that are owned, operated, and/or located by distinct and wholly-unrelated companies (e.g., competitors in the healthcare industry for the transmission rights to the healthcare transactions and the revenue associated therewith).

It will be appreciated that while the third-party switch provider computer 112 is presented as a single processor-driven device, the third-party switch provider computer 112 may also be two or more distinct processor-driven devices for performing the respective operations. The example third-party switch provider computer 112 may include computer-executable instructions for receiving and processing healthcare transactions, and/or healthcare transaction data from a pharmacy computer 104 or service provider computer 106.

Similar to other components of the system 100, the third-party switch provider computer 112 may include one or more processors 178, one or more memory devices 180, one or more I/O interfaces 182, and one or more network interfaces 184. The one or more memory devices 180 may be any suitable memory devices, for example, caches, read only memory devices, random access memory devices, magnetic storage devices, removable memory devices. The one or more memory devices may store data, executable instructions, and/or various program modules utilized by the third-party switch provider computer 112, for example, data files 186, an OS 188, a DBMS 190, and a host module 192. The data files 186 may include any suitable information that is utilized by the third-party switch provider computer 112 to receive, process, analyze, and/or store healthcare transactions. The OS 188 may be a suitable software module that controls the general operation of the particular third-party switch provider computer 112. The OS 188 may also facilitate the execution of other software modules by the one or more processors 178, for example, the DBMS 190 and/or the host module 192. The OS 188 may be any currently existing or future-developed operating system including, but not limited to, Microsoft Windows®, Apple OSX™, Linux, Unix, or a mainframe operating system.

The DBMS 190 may be a suitable software module that facilitates access and management of one or more databases, that are utilized to store information that is received by or utilized by the third-party switch provider computer 112. The host module 192 may initiate, receive, process, analyze, store, and/or respond to requests, such as the receipt of healthcare transactions from the host module 154 of the service provider computer 106, the client module 138 of the pharmacy computer 104, or the host module 172 of the claims processor computer 108. The third-party switch provider computer 112 may include additional program modules as desired. Those of ordinary skill in the art will appreciate that the third-party switch provider computer 112 may include alternate and/or additional components, hardware or software without departing from example embodiments disclosed herein.

The one or more I/O interfaces 182 may facilitate communication between the third-party switch provider computer 112 and one or more input/output devices, for example, one or more user interface devices, such as a keyboard, mouse, display, keypad, control panel, touchscreen display, remote control, microphone, etc. that facilitate user interaction with the third-party switch provider computer 112. The one or more network interfaces 184 may facilitate connection of the third-party switch provider computer 112 to one or more suitable networks, for example, the network 110. In this regard, the third-party switch provider computer 112 may receive healthcare transactions, healthcare transaction data, and/or other communications from the service provider computer 106, the pharmacy computer 104, and/or the claims processor computer 108.

The database 196, of FIG. 1, represents one or more databases that can be locally or remotely distributed with respect to the service provider computer 106 and/or the service provider network monitoring module 194. The database 196 may be operable to store information associated with various patients, pharmacies, pharmacy computers 104, payers, claims processor computers 108, third-party switch provider computers 112, and/or from various healthcare transactions that have been received by the service provider computer 106 and/or adjudicated healthcare transaction response adjudicated by the claims processor computer 106. The database 196 may also receive, store, and provide, as needed, healthcare transactions data and network status data for the third-party switch computers 112 from the service provider computer 106 and/or the service provider network monitoring module 194. In certain exemplary embodiments, the healthcare transactions data includes all or any portion of the data included in healthcare transactions received by the service provider computer 106 from one or more pharmacy computers 104 and/or adjudicated responses to healthcare transactions from one or more claims processor computers 108. In addition, the database 196 or another database may include a table, schedule, or listing correlating payer identifiers to one of i) exclusively receiving healthcare transactions from the third-party switch provider computer; ii) exclusively receiving healthcare transactions from the service provider computer; and iii) can receive healthcare transactions from both the service provider computer and the third-party switch provider computer. Further the database 196 or another database may include a table, schedule, or listing correlating pharmacy identifiers to the intermediary the each pharmacy has contracted with (either the service provider computer 106 or one of the third-party switch computers 112) to receive healthcare transactions from the respective pharmacy and to pass those healthcare transactions along the to the identified claims processor computer 108. Further, the database 196 or another database may include threshold limits (e.g., time threshold for time-outs to the third-party switch provider computer 112, one or more thresholds for percentage and/or number of transactions timed-out, non-responsive, or rejected by the third-party switch provider computer 112 for determining that the third-party switch provider computer 112 is not currently operating properly and needs to be bypassed, and corresponding thresholds for determining when the third-party switch provider computer 112 is once-again operating properly), and counters for determining the number or percentage of times a transmission from the service provider computer 106 to the third-party switch provider computer 112 fails or is successful.

With continued reference to FIG. 1, the claims processor computer 108 may be any suitable processor-driven device that facilitates receiving, processing, and/or fulfilling healthcare transactions, such as predetermination of benefits transactions, healthcare claim transactions, prescription claim or billing requests, healthcare order transactions, or e-prescription transactions (e.g., electronic prescription order transactions, e-scripts, or e-prescriptions) received from the service provider computer 106. For example, the claims processor computer 108 may be a processor-driven device associated with one or more PBMs, insurers, government payers, Medicare Part D payers, accountable care organizations, or claims clearinghouses. As desired, the claims processor computer 108 may include any number of special purpose computers or other particular machines, application-specific circuits, microcontrollers, personal computers, minicomputers, mainframe computers, servers, and the like.

In certain exemplary embodiments, the operations of the claims processor computer 108 may be controlled by computer-executed or computer-implemented instructions that are executed by one or more processors associated with the claims processor computer 108 to form a special-purpose computer or other particular machine that is operable to facilitate the receipt, processing, and/or fulfillment of healthcare transactions received from the service provider computer 106. The one or more processors that control the operations of the claims processor computer 108 may be incorporated into the claims processor computer 108 and/or in communication with the claims processor computer 108 via one or more suitable networks. In certain embodiments, the operations and/or control of the claims processor computer 108 may be distributed amongst several processing components.

Similar to other components of the system 100, the claims processor computer 108 may include one or more processors 158, one or more memory devices 160, one or more input/output ("I/O") interfaces 162, and one or more network interfaces 164. The one or more memory devices 160 may be any suitable memory devices, for example, caches, read-only memory devices, random access memory devices, magnetic storage devices, removable memory devices. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare transactions, for example, patient profiles, patient insurance information, other information associated with a patient, information associated with a healthcare provider, etc. The operating system OS 168 may be a suitable software module that controls the general operation of the claims processor computer 108. The OS 168 may also facilitate the execution of other software modules by the one or more processors 158, for example, the DBMS 170 and/or the host module 172. The OS 168 may be any currently existing or future-developed operating system including, but is not limited to, Microsoft Windows®, Apple OSX™, Linux, Unix, or a mainframe operating system.

The DBMS 170 may be a suitable software module that facilitates access and management of one or more databases that are utilized to store information that is utilized by the claims processor computer 108 in various example embodiments. The host module 172 may initiate, receive, process, and/or respond to requests, such as healthcare transactions or claim requests, from the host module 154 of the service provider computer 106 or a host module 192 of a third-party switch provider computer 112. The claims processor computer 108 may include additional program modules for performing other pre-processing or post-processing methods described herein. Those of ordinary skill in the art will appreciate that the claims processor computer 108 may include alternate and/or additional components, hardware or software without departing from the example embodiments described herein.

The one or more I/O interfaces 162 may facilitate communication between the claims processor computer 108 and one or more input/output devices, for example, one or more user interface devices, such as a display, keypad, keyboard, mouse, control panel, touch screen display, remote control, microphone, etc. that facilitate user interaction with the claims processor computer 108. The one or more network interfaces 164 may facilitate connection of the claims processor computer 108 to one or more suitable networks, for example, the network 110. In this regard, the claims processor computer 108 may receive healthcare transactions and/or other communications from the service provider computer 106 and/or the third-party switch provider computer 112, and the claims processor computer 108 may communicate information associated with processing the healthcare transactions to the service provider computer 106 and/or the third-party switch provider computer 112.

The network 110 may include any telecommunication and/or data network, whether public, private, or a combination thereof, including a local area network, a wide area network, an intranet, the Internet, intermediate hand-held data transfer devices, and/or any combination thereof and may be wired and/or wireless. The network 110 may also allow for real-time, off-line, and/or batch transactions to be transmitted between or among the pharmacy computer 104, the service provider computer 106, the third-party switch provider computer 112, the service provider network monitoring module 194, the database 196, and/or the claims processor computer 108. Due to network connectivity, various methodologies, as described herein may be practiced in the context of distributed computing environments. Although the service provider computer 106 is shown for simplicity as being in communication with the pharmacy computer 104, the third-party switch provider computer 112, the service provider network monitoring module 194, the database 196, and/or the claims processor computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment. For example, the service provider computer 106 may form the basis of network 110 that interconnects one or more of the pharmacy computers 104, the third-party switch provider computers 112, the service provider network monitoring module 194, the database 196, and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one exemplary embodiment, the service provider computer 106 (or other computer) may be implemented as a specialized processing machine that includes hardware and/or software for performing the methods described herein. Accordingly, the exemplary embodiments described herein should not be construed as being limited to any particular operating environment, system architecture, or device configuration.

Operational Overview

Figure 2:
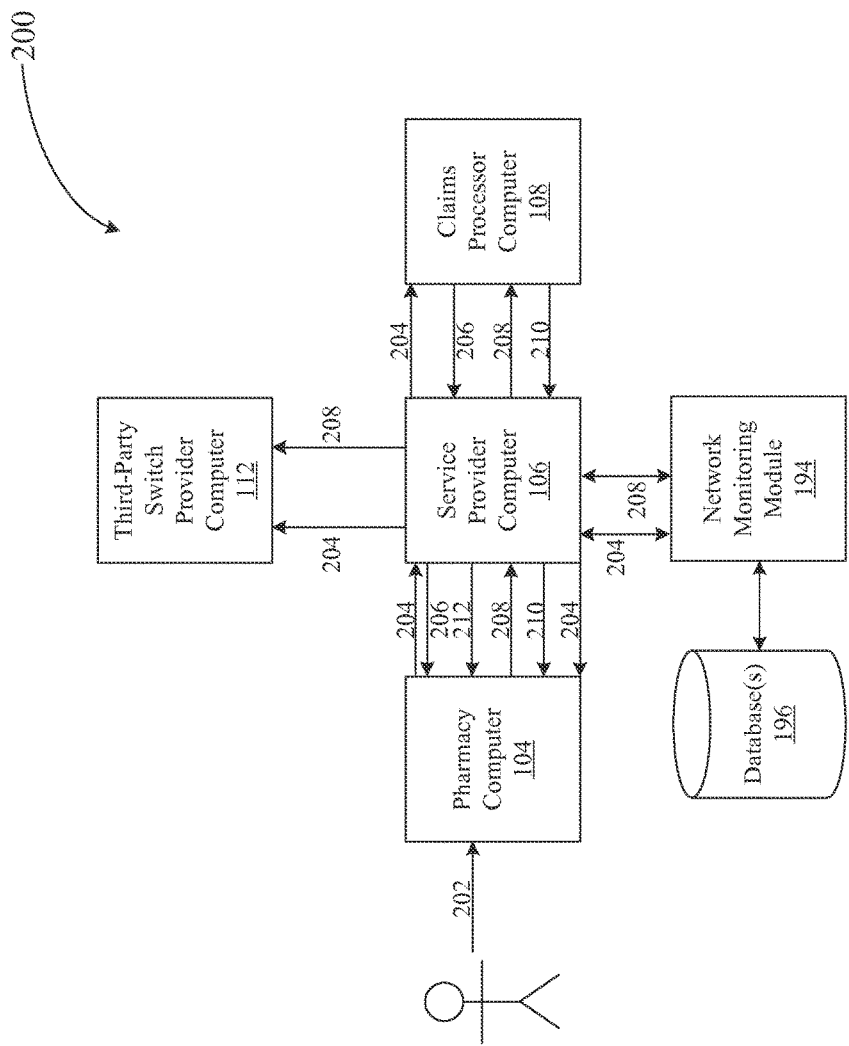
FIG. 2 is a diagram of an example data flow for determining operational status of third-party switch provider systems for receipt and processing of electronically submitted healthcare transactions as part of the processing of a healthcare transaction processed through a service provider computer, according to one exemplary embodiment.
Figure 3A:
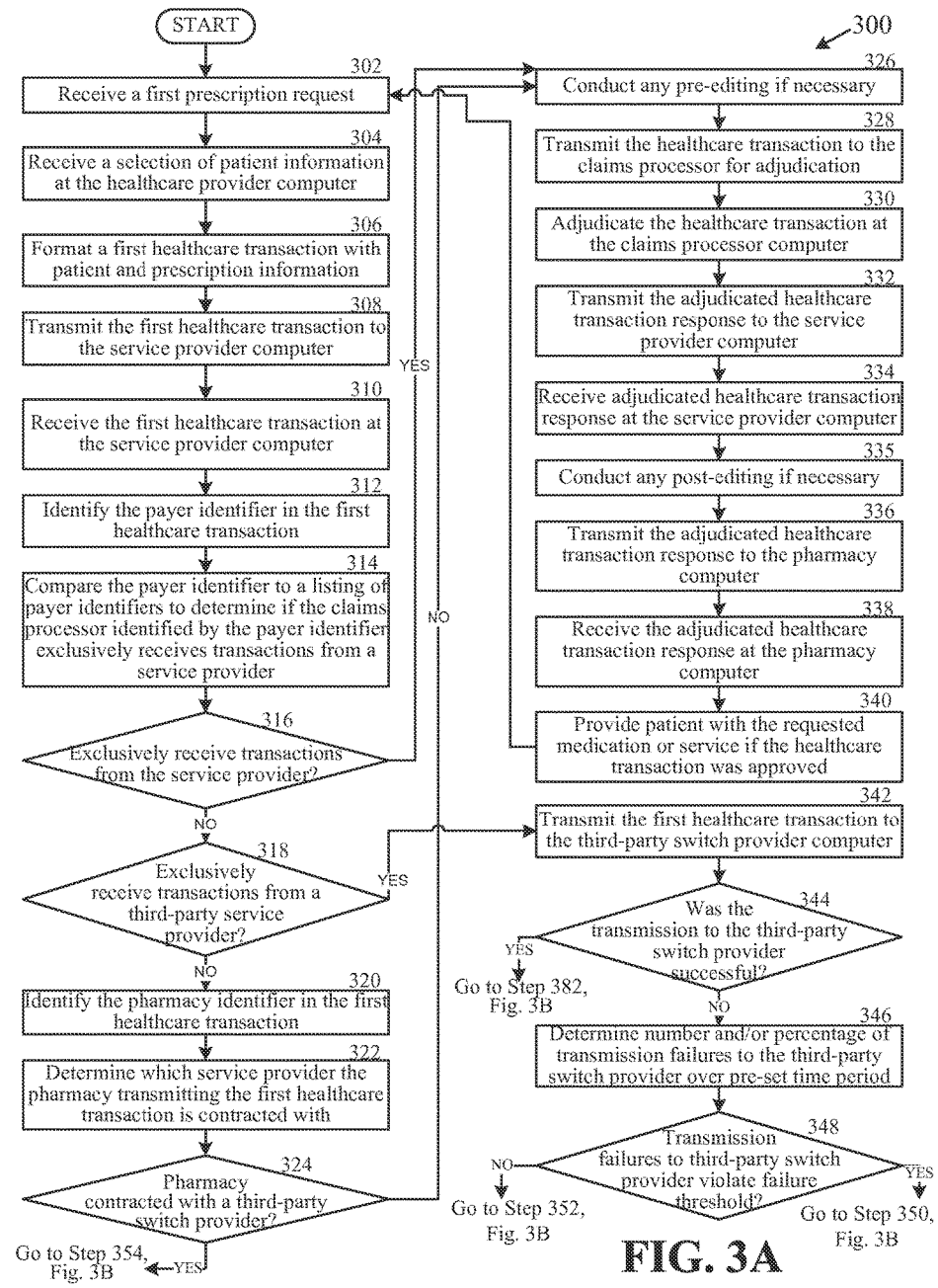
FIGS. 3A and 3B are a flow chart of an example method for determining if a third-party switch provider system is no longer operating or otherwise processing electronically submitted healthcare transactions as part of the processing of electronically submitted healthcare transactions processed through a service provider computer, according to one exemplary embodiment of the disclosure.
Figure 3B:
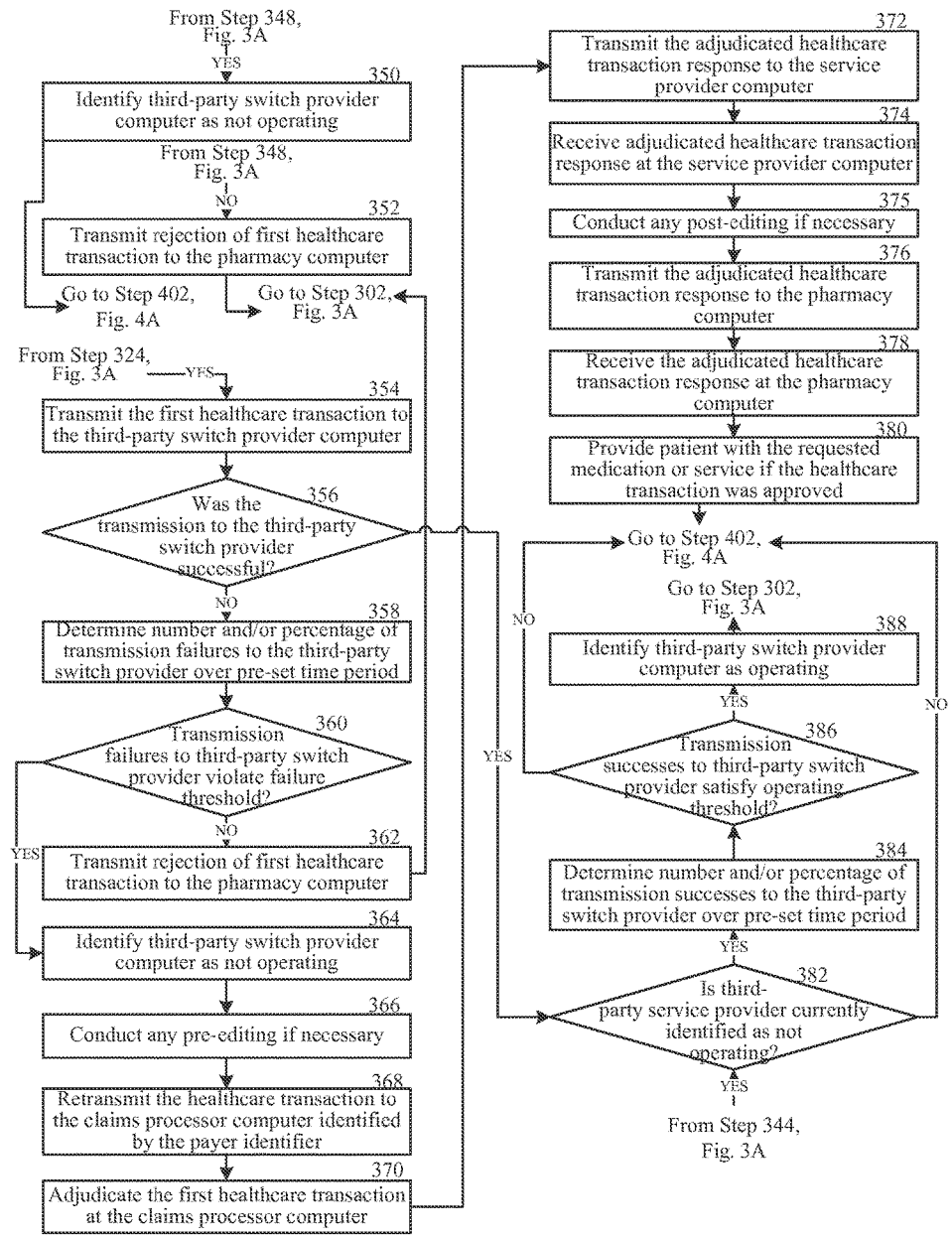

FIG. 2 is a diagram of one example data flow 200 for determining operational status of third-party switch provider computers 112 for receipt and processing of electronically transmitted healthcare transactions, according to one example embodiment of the disclosure. FIGS. 3A-B are a flow chart of an example method 300 for determining if a third-party switch provider computer 112 is no longer operating or otherwise processing electronically submitted healthcare transactions, in accordance with one exemplary embodiment. The exemplary method 300, described below, may be performed by a suitable service provider computer 106 and/or service provider network monitoring module 194. The exemplary methods 300-400 will be described with reference to a pharmacy as the healthcare provider; however, this is only for purposes of example as other healthcare providers could be substituted for, and should each be individually read as being a part of each of these methods. As such, where the discussion of the methods below and the drawings state a pharmacy, any other healthcare provider could be substituted, such as a physician, hospital, physician's office, clinic, prescriber of the medication, or healthcare center.

In addition, the exemplary methods 300-400 described below will be described with reference to a healthcare claim transaction as the healthcare transaction; however, this also is only for purposes of example as other healthcare transactions (which may include, for example, a predetermination of benefits transaction, the healthcare claim transaction, prescription claim or billing request, healthcare order transaction, or e-prescription transaction (e.g., electronic prescription order transaction, e-script, or e-prescription)) could be substituted for the healthcare claim transaction and each form of healthcare transaction should each individually be read as being used in the methods described below.

Referring now to FIGS. 1, 2, 3A, and 3B, the exemplary method 300 begins at the START step and proceeds to step 302, where a first prescription request 202 is received. In one example embodiment, the first prescription/order request 202 is received by a pharmacist at a pharmacy. The first prescription/order request 202 may be received from a patient, another healthcare provider prescribing a medication or service (e.g., physician, hospital, etc.), by phone, via the Internet, via an electronic prescription or by way of an electronic system order. For example, the first prescription 202 may be received by the patient from a prescriber of the medication, such as a doctor, dentist, nurse, physician's assistant, or any other person legally permitted to prescribe medication under applicable state and/or federal laws. The patient may go to the location of the pharmacy and physically hand the first prescription request 202 to the pharmacist or make a request via a web portal communicably coupled to the pharmacy computer 104 or an IVR communicably coupled to the pharmacy computer 104. The pharmacist determines the patient's name and accesses the pharmacy computer 104, which receives a selection of patient information from the pharmacist via the I/O interface 128 in step 304. For example, the pharmacist accesses the pharmacy computer 104 and accesses a database of patient information, which may be stored in memory 126 or in another database either local or remote from the pharmacy computer 104. The pharmacist can then select the name or other patient identification information in the patient information database that matches the name or other identification information of the patient.

In step 306, a first electronically transmittable healthcare claim transaction 204 is generated and/or formatted at the pharmacy computer 104. In certain exemplary embodiments, the pharmacy computer 104 formats the first healthcare claim transaction 204 with patient information and prescription information. All or a portion of the information in the first healthcare claim transaction 204 can be input into the first healthcare claim transaction 204 by the pharmacist via the I/O interface 128. According to one example embodiment, the first healthcare claim transaction 204 may be formatted in accordance with a version of the National Council for Prescription Drug Programs (NCPDP) Telecommunication Standard, although other standards may be utilized as well. As desired, the first healthcare claim transaction 204 may include a Banking Identification Number (BIN Number), a Processor Control Number (PCN), and/or a Group ID ("payer identifier") for identifying a particular claims processor computer (e.g., PBM, payer, insurance company, Medicare, Medicaid, or other government healthcare insurance payer, accountable care organization, etc.), such as the claims processor computer 108, as a destination for the first healthcare claim transaction 204. In addition, the first healthcare claim transaction 204 may also include information relating to the patient, payer, prescriber, healthcare provider, and/or the requested medication/product/service. As an example, the first healthcare transaction 204 may include one or more of the following information:

Payer ID/Routing Information
BIN Number (i.e., Banking Identification Number), BIN Number and Processor Control Number (PCN), and/or BIN Number and Group ID that designates a destination of the healthcare transaction 204
Patient Information
Name (e.g., Patient Last Name, Patient First Name, etc.)
Date of Birth of Patient
Age of Patient
Gender
Patient Address (e.g., Street Address, Zip Code, etc.)
Patient Contact Information (e.g., patient telephone number, email address, etc.)
Patient Health Condition Information
Patient ID or other identifier
Insurance/Coverage Information
Cardholder Name (e.g., Cardholder First Name, Cardholder Last Name)
Cardholder ID and/or other identifier (e.g., person code)
Group ID and/or Group Information
Prescriber Information
Primary Care Provider ID or other identifier (e.g., NPI code)
Primary Care Provider Name (e.g., Last Name, First Name)
Prescriber ID or other identifier (e.g., NPI code, DEA number)
Prescriber Name (e.g., Last Name, First Name)
Prescriber Contact Information (e.g., Telephone Number, Facsimile Number, Email Address, etc.)
Pharmacy or other Healthcare Provider Information (e.g., store name, chain identifier, etc.)
Pharmacy or other Healthcare Provider ID (e.g., NPI code)
Claim Information
Drug, service, or product identifier/information (e.g., name of the medication/product/service, National Drug Code (NDC) code, RxNorm code, etc.)
Prescription/Service Reference Number (e.g., a value assigned to the healthcare transaction by the healthcare provider's computer system to identify the healthcare transaction from other transactions submitted by the healthcare provider)
Date Prescription Written
Quantity Dispensed
Days' Supply
Diagnosis/Condition
Pricing information for the drug/service/product (e.g., network price, Usual & Customary price)
Number of Refills Authorized
One or more NCPDP Message Fields
One or more Drug Utilization (DUR) Codes Date of Service (submission time) (may include both the date and the time the transaction was submitted to the network by the healthcare provider).

The first healthcare claim transaction 204 can be used to determine if the claims processor associated with the claims processor computer 106 approves or rejects payment coverage for medication, product, or service being requested in the first healthcare claim transaction 204 and, if approved, the amount the claims processor will cover (or pay) for the medication, product or service being requested and how much the patient co-pay amount will be.

The healthcare provider computer 104 electronically transmits the first healthcare claim transaction 204 to the service provider computer 106 in step 308. In step 310, the service provider computer 106 receives the first healthcare claim transaction 204. For example, the first healthcare claim transaction 204 can be electronically transmitted by the healthcare provider computer 104 to the service provider computer 106 through the network 110. In step 312, the service provider computer 106 and/or the service provider network monitoring module 194 can determine the payer identifier in the first healthcare claim transaction 204. For example, the payer identifier can be the BIN Number, BIN Number and PCN, or the BIN Number and Group ID provided in the first healthcare claim transaction 204. The service provider network monitoring module 194 or another portion of the service provider computer 106 can parse the first healthcare transaction 204 to identify the fields of the transaction 204 that include this information.

In step 314, the service provider network monitoring module 194 or another portion of the service provider computer 106 can compare the payer identifier from the transaction 204 to a listing of payer identifiers to determine if the claims processor computer identified by the payer identifier exclusively receives healthcare transactions from one of the intermediaries/switch provider/service providers. For example, the service provider network monitoring module 194 or another portion of the service provider computer 106 can compare the payer identifier to the listing to determine if a match exists, and based on that matching record, determine if the claims processor exclusively receives healthcare transactions from only one switch provider/service provider. In step 316, an inquiry is conducted to determine, based on the review in step 314, if the claims processor identified by the payer identifier exclusively receives healthcare transactions (such as healthcare claim transaction 204) from the service provider computer 106. In one example, the determination is made by the service provider network monitoring module 194 or another portion of the service provider computer 106. If there is no exclusive arrangement between the claims processor identified by the payer identifier and the service provider computer 106, the NO branch is followed to step 318. Otherwise, the YES branch is followed to step 326.

In step 326, the service provider computer 106 conducts any pre-editing, if necessary, on the first healthcare claim transaction 204. The pre-edits may include verifying, adding, and/or editing information included in the first healthcare claim transaction 204 prior to it being communicated to a claims processor computer 108. For example, the service provider computer 106 can parse the first healthcare claim transaction 204 to determine if the Patient ZIP/Postal Code was submitted and if it is valid. The service provider computer 106 electronically transmits the first healthcare claim transaction 204 to the claims processor computer 108 in step 328. For example, a first healthcare claim transaction 204 can be transmitted from the service provider computer 106 to the claims processor computer 108 via the network 110. The claims processor computer 108 receives and adjudicates the first healthcare claim transaction 204 in step 330 to determine if the patient has coverage, to determine to what extent the patient's coverage covers the requested medication/product/service identified in the transaction 204, and to generate an adjudication 206 as to whether the transaction 204 is approved or rejected. Typically, if the transaction 204 is approved, the adjudicated response 206 provides the amount of the cost of the medication that will be covered by the claims processor/payer and the patient co-pay and if rejected, the adjudicated response 206 provides the reason for the rejection (e.g., prior authorization required, patient not covered, medication not covered, etc.). Example adjudications can include, but are not limited to, accepted, approved, paid, captured, denied, and denied with request for additional information and resubmission. In certain exemplary embodiments, the adjudication can be input into a field of the first healthcare claim transaction 204 that is recognized by the service provider computer 106 and/or the healthcare provider computer 104. In step 332, the claims processor computer 108 electronically transmits the adjudicated first healthcare claim transaction response 206 to the service provider computer 106 via, for example, the network 110.

The service provider computer 106 receives the adjudicated first healthcare claim transaction response 206 from the claims processor computer 108 in step 334. In step 335, the service provider computer 106 and/or the network monitoring module 194 may conduct any post-editing to the adjudicated healthcare claim transaction response 206, if necessary, prior to sending the response 206 along to the pharmacy computer 104. In step 336, the service provider computer 106 electronically transmits the adjudicated first healthcare claim transaction response 206 to the pharmacy computer 104. In one exemplary embodiment, the adjudicated response 206 is transmitted to the pharmacy computer 104 via the network 110. The adjudicated first healthcare claim transaction response 206 is received at the pharmacy computer 104 in step 338. The pharmacist or other pharmacy employee may provide the patient with the medication requested in the first healthcare claim transaction 204 upon receipt of any necessary patient co-pay or may explain the reasons for the transaction 204 being rejected during adjudication in step 340. The process then continues to FIG. 4 for receipt and processing of additional healthcare transactions by the service provider computer 106.

Returning to step 318, an inquiry is conducted to determine, based on the review in step 314, if the claims processor identified by the payer identifier exclusively receives healthcare transactions (such as healthcare claim transaction 204) from the third-party switch provider computer 112 or another intermediary computing system. In one example, the determination is made by the service provider network monitoring module 194 or another portion of the service provider computer 106. If there is no exclusive arrangement, the NO branch is followed to step 320. If there is an exclusive arrangement between the claims processor identified by the payer identifier and the third-party switch provider computer 112, the YES branch is followed to step 342.

In step 342, the service provider computer 106 electronically transmits the healthcare claim transaction 204 to the third-party switch provider computer 112. In one example, the transmission from the service provider computer 106 to the third-party switch provider computer 112 of the transaction 204 may be via the network 110. In step 344, an inquiry is conducted to determine if the transmission of the transaction 204 to the third-party switch provider computer 112 was successful. In one example embodiment, the determination may be made by the service provider network monitoring module 194 or another portion of the service provider computer 106. For example, the transmission would not be successful, if the transmission is rejected by the third-party switch provider computer 112, if there is no response from the third-party switch provider computer 112 to the service provider computer 106 regarding the transmission, or if the transmission times out (e.g., no response received from the third-party switch provider computer 112 by the service provider computer 106 within a predetermined time threshold of sending the transmission. In one example embodiment, the predetermined time threshold is configurable and in certain example embodiments is 15 seconds, however, any other time period between 0-300 seconds (including between 0-1000 milliseconds or any other fractions of a second(s) therein) is also possible. If the transmission to the third-party switch provider computer 112 was successful, the YES branch is followed to step 382. Otherwise, the NO branch is followed to step 346.

In an alternative example embodiment, in the inquiry of step 344, the transmission of the healthcare claim transaction 204 to the third-party switch provider computer 112 is not successful when the third-party switch provider computer 112 sends back a response to the service provider computer 106 indicating that the third-party switch provider computer 112 is not able to process the healthcare claim transaction 204. The response may indicate that the third-party switch provider computer 112 is under an outage or partial outage or that failure of the third-party switch provider computer 112 is about to occur. In this alternative embodiment, if a response from the third-party switch provider computer 112 indicating a problem with the system 112 is not received by the service provider computer 106, the network monitoring module 194 or another portion of the service provider computer 106 will presume that the third-party switch provider computer 112 is operating properly. In this alternative embodiment, if a response is received indicating that the third-party switch provider computer 112 has a problem, steps 346-348 may be skipped and the method may proceed to step 350. If no response from the third-party switch provider computer 112 indicating a problem with the computer 112 is received by the service provider computer 106, the method may continue to step 382.

In step 346, the service provider network monitoring module 194 or another portion of the service provider computer 106 determines the number and/or percentage of transmission failures that have occurred between the service provider computer 106 and the third-party switch provider computer 112 over a pre-set time period. In one example, embodiment, the pre-set time period is configurable based on the needs of the system administrator. In one example, the pre-set time period can be 5 minutes, however, any other time period between 0-120 minutes is contemplated within the scope of the disclosure. In one example embodiment, each time a transmission to the third-party switch is not successful, the service provider network monitoring module 194 or another portion of the service provider computer 106 can increment a counter variable in the database 196. The failure counter may be further associated with a timer to keep count of a number of failed transmissions over the pre-set time period. In addition, a counter variable may be maintained in the database 196 for all of the transactions sent from the service provider computer 106 to the third-party switch provider computer 112 in order to determine a percentage of transmission failures rather than or in addition to the number of transmission failures over the pre-set time period.

In step 348, an inquiry is conducted to determine if the transmission failures to the third-party switch provider computer 112 violate the failure threshold. In one example embodiment, the determination can be made by the service provider network monitoring module 194 or another portion of the service provider computer 106. For example, the service provider network monitoring module may obtain the configurable failure threshold from the database 196 and can compare that to the number and/or percentage of transmission failures identified in step 346. In one example, a single non-response or timeout within fifteen seconds of a healthcare claim transaction that is not exclusively received from a third-party service provider may meet the failure threshold. In another example embodiment, if responses to a series of healthcare transactions being sent to the third-party switch provider computer 112 are received in the range of 5-15 seconds for greater than a minute, the failure threshold may be considered to have been met as the third-party switch provider computer 112 is exhibiting symptoms (slow response times) of a system that is about to fail. In yet another example embodiment, if rejections or time-outs for a series of healthcare claim transactions sent to the third-party switch provider computer 112 reach a level equal to about 20 percent of the healthcare claim transactions being sent to the third-party switch provider computer by the service provider computer 106, the failure threshold may be considered to have been met as the high rate of rejections/timeouts is indicative of a partial outage of the third-party switch provider computer 112. If the number and/or percentage of transmission failures violates (e.g., is greater than or is greater than or equal to the failure threshold) the failure threshold, then the YES branch can be followed to step 350, where the service provider network monitoring module 194 or another portion of the service provider computer 106 can designate or otherwise determine that the third-party switch provider computer 112 is not operating (e.g., not receiving and processing healthcare transactions at a normal rate). The process can then proceed to FIG. 4. Returning to step 348, if the number and/or percentage of transmissions does not violate (e.g., is less than or less than or equal to the failure threshold) the failure threshold, the NO branch is followed to step 352, where the service provider computer 106 electronically transmits the rejection of the first healthcare transaction to the pharmacy computer 104 via, for example, the network 110. The process then proceeds to step 302 for the receipt of subsequent healthcare transactions from the one or more pharmacy computers 104.

Returning to step 318, when the determination is that the payer identifier does not identify a claims processor computer 108 that exclusively receives transactions from the third-party switch provider computer 112, the NO branch is followed to step 320. In step 320, the service provider network monitoring module 194 or another portion of the service provider computer 106 identifies the pharmacy identifier in the first healthcare transaction 204. In one example, the pharmacy identifier can be the NPI code, pharmacy name of pharmacy number within a pharmacy chain. In step 322, the service provider network monitoring module 194 or another portion of the service provider computer 106 can determine which intermediary switch/service provider (e.g., one of the service provider computer 106 or the third-party switch provider computer 112) the pharmacy identified by the pharmacy identifier in the first healthcare transaction 204 is contracted with to receive healthcare transactions and pass those healthcare transactions on to the proper claims processor computer. For example, the service provider network monitoring module 194 or another portion of the service provider computer 106 may compare the pharmacy identifier from the first healthcare transaction to a table, listing, or schedule of pharmacy identifiers to identify a matching pharmacy identifier in a record, such as in the database 196. Based on the matching record (e.g., record states which intermediary is contracted with or records are organized by which intermediary the pharmacies are contracted with), the service provider network monitoring module 194 or another portion of the service provider computer 106 can determine which intermediary switch/service provider the pharmacy is contracted with.

In step 324, an inquiry is conducted to determine if the pharmacy identified by the pharmacy identifier in the first healthcare transaction 204 is contracted with the third-party switch provider computer 112. As discussed above, the determination may be made by the service provider network monitoring module 194 or another portion of the service provider computer 106. If the identified pharmacy is not contracted with the third-party switch provider computer 112, the NO branch is followed to step 326 for processing as discussed above. Otherwise, the YES branch is followed to step 354.

In step 354, the service provider computer 106 electronically transmits the healthcare claim transaction 204 to the third-party switch provider computer 112. In one example, the transmission from the service provider computer 106 to the third-party switch provider computer 112 of the transaction 204 may be via the network 110. In step 356, an inquiry is conducted to determine if the transmission of the transaction 204 to the third-party switch provider computer 112 was successful. In one example embodiment, the determination may be made by the service provider network monitoring module 194 or another portion of the service provider computer 106. For example, the transmission would not be successful, if the transmission is rejected by the third-party switch provider computer 112, if there is no response from the third-party switch provider computer 112 to the service provider computer 106 regarding the transmission, or if the transmission times out (e.g., no response received from the third-party switch provider computer 112 by the service provider computer 106 within a predetermined time threshold of sending the transmission. In one example embodiment, the predetermined time threshold is configurable and in certain example embodiments is 15 seconds, however, any other time period between 0-300 seconds (including between 0-1000 milliseconds or any other fractions of a second(s) therein) is also possible. If the transmission to the third-party switch provider computer 112 was successful, the YES branch is followed to step 382. Otherwise, the NO branch is followed to step 358.

In an alternative example embodiment, in the inquiry of step 356, the transmission of the healthcare claim transaction 204 to the third-party switch provider computer 112 is not successful when the third-party switch provider computer 112 sends back a response to the service provider computer 106 indicating that the third-party switch provider computer 112 is not able to process the healthcare claim transaction 204 (e.g., the third-party switch provider computer 112 is down, experiencing an outage or partial outage or is otherwise not operating properly). The response may indicate that the third-party switch provider computer 112 is under an outage or partial outage or that failure of the third-party switch provider computer 112 is about to occur. In this alternative embodiment, if a response from the third-party switch provider computer 112 indicating a problem with the system 112 is not received by the service provider computer 106, the network monitoring module 194 or another portion of the service provider computer 106 will presume that the third-party switch provider computer 112 is operating properly. In this alternative embodiment, if a response is received indicating that the third-party switch provider computer 112 has a problem, steps 358-362 may be skipped and the method may proceed to step 364. If no response from the third-party switch provider computer 112 indicating a problem with the computer 112 is received by the service provider computer 106, the transmission of the healthcare claim transaction 204 is presumed to have been successful and the method may continue to step 382.

In step 358, the service provider network monitoring module 194 or another portion of the service provider computer 106 determines the number and/or percentage of transmission failures that have occurred between the service provider computer 106 and the third-party switch provider computer 112 over a pre-set time period. In one example, embodiment, the pre-set time period is configurable based on the needs of the system administrator. In one example, the pre-set time period can be 5 minutes, however, any other time period between 0-120 minutes is contemplated within the scope of the disclosure. In one example embodiment, each time a transmission to the third-party switch 112 is not successful, the service provider network monitoring module 194 or another portion of the service provider computer 106 can increment a counter variable in the database 196. The failure counter may be further associated with a timer to keep count of a number of failed transmissions over the pre-set time period. In addition, a counter variable may be maintained in the database 196 for all of the transactions sent from the service provider computer 106 to the third-party switch provider computer 112 in order to determine a percentage of transmission failures rather than or in addition to the number of transmission failures over the pre-set time period.

In step 360, an inquiry is conducted to determine if the transmission failures to the third-party switch provider computer 112 violate the failure threshold. In one example embodiment, the determination can be made by the service provider network monitoring module 194 or another portion of the service provider computer 106. For example, the service provider network monitoring module may obtain the configurable failure threshold from the database 196 and can compare that to the number and/or percentage of transmission failures identified in step 358. If the number and/or percentage of transmission failures violates (e.g., is greater than or is greater than or equal to the failure threshold) the failure threshold, then the YES branch can be followed to step 364, where the service provider network monitoring module 194 or another portion of the service provider computer 106 can designate or otherwise determine that the third-party switch provider computer 112 is not operating (e.g., not receiving and processing healthcare transactions at a normal rate).

In step 366, due to the fact that the third-party switch provider 112 is not operating, the service provider computer 106 begins operating as the intermediary switch/service provider for the pharmacies contracted with the third-party switch provider computer 112 while it is not operating so that those pharmacies will still be able to have their healthcare transactions adjudicated in a real-time or near real-time manner. As such, the service provider computer 106 conducts any pre-editing, if necessary, on the first healthcare claim transaction 204. The pre-edits may include verifying, adding, and/or editing information included in the first healthcare claim transaction 204 prior to it being communicated to a claims processor computer 108. For example, the service provider computer 106 can parse the first healthcare claim transaction 204 to determine if the Patient ZIP/Postal Code was submitted and if it is valid. The service provider computer 106 electronically retransmits the first healthcare claim transaction 204 to the claims processor computer 108 identified by the payer identifier in the transaction 204 in step 368. For example, the service provider network monitoring module 194 or another portion of the service provider computer 106 identifies the payer identifier in the transaction 204 and determines the claims processor computer to transmit the transaction based on the payer identifier. The first healthcare claim transaction 204 can then be transmitted from the service provider computer 106 to the claims processor computer 108 via the network 110. The claims processor computer 108 receives and adjudicates the first healthcare claim transaction 204 in step 370 to determine if the patient has coverage, to determine to what extent the patient's coverage covers the requested medication/product/service identified in the transaction 204, and to generate an adjudication 206 as to whether the transaction 204 is approved or rejected. In certain example embodiments, the adjudication can be input into a field of the first healthcare claim transaction 204 that is recognized by the service provider computer 106 and/or the healthcare provider computer 104. In step 372, the claims processor computer 108 electronically transmits the adjudicated first healthcare claim transaction response 206 to the service provider computer 106 via, for example, the network 110.

The service provider computer 106 receives the adjudicated first healthcare claim transaction response 206 from the claims processor computer 108 in step 374. In step 375, the service provider computer 106 and/or the network monitoring module 194 may conduct any post-editing to the adjudicated healthcare claim transaction response 206, if necessary, prior to sending the response 206 along to the pharmacy computer 104. In step 376, the service provider computer 106 electronically transmits the adjudicated first healthcare claim transaction response 206 to the pharmacy computer 104. In one exemplary embodiment, the adjudicated response 206 is transmitted to the pharmacy computer 104 via the network 110. The adjudicated first healthcare claim transaction response 206 is received at the pharmacy computer 104 in step 378. The pharmacist or other pharmacy employee may provide the patient with the medication requested in the first healthcare claim transaction 204 upon receipt of any necessary patient co-pay or may explain the reasons for the transaction 204 being rejected during adjudication in step 380. The process may then continue to FIG. 4 for receipt and processing of additional healthcare transactions by the service provider computer 106.

Returning to step 360, if the number and/or percentage of transmissions does not violate (e.g., is less than or less than or equal to the failure threshold) the failure threshold, the NO branch is followed to step 362, where the service provider computer 106 electronically transmits the rejection of the first healthcare transaction 204 to the pharmacy computer 104 via, for example, the network 110. The process then proceeds to step 302 for the receipt of subsequent healthcare transactions from the one or more pharmacy computers 104.

Returning to step 356, if the transmission to the third-party switch provider computer 112 was successful, the YES branch is followed to step 382. In step 382, an inquiry is conducted to determine if the third-party switch provider computer 112 is currently identified as not operating. In one example embodiment, the determination can be made by the service provider network monitoring module 194 or another portion of the service provider computer 106. For example, the identification of the operating status for the third-party switch provider computer 112 may be stored and accessed from the database 112 and/or memory 142 and can be looked up by the service provider network monitoring module 194 or another portion of the service provider computer 106. If the third-party switch provider computer 112 is currently identified as operating, the NO branch is followed to FIG. 4. Otherwise, the YES branch is followed to step 384, where the service provider network monitoring module 194 or another portion of the service provider computer 106 can determine the number and/or percentage of transmission successes to the third-party switch provider computer 112 over a pre-set time period.

Similar to that described in step 346, with reference to determining the number of transmission failures, the number of transmission successes to the third-party switch provider computer 112 can be similarly determined. In one example, embodiment, the pre-set time period is configurable based on the needs of the system administrator. In one example, the pre-set time period can be 5 minutes, however, any other time period between 0-120 minutes is contemplated within the scope of the disclosure. In one example embodiment, each time a transmission to the third-party switch provider computer 112 is successful, the service provider network monitoring module 194 or another portion of the service provider computer 106 can increment a counter variable in the database 196 or other memory. The successful transmission counter may be further associated with a timer to keep count of a number of successful transmissions to the third-party switch provider computer 112 over the pre-set time period. In addition, a counter variable may be maintained in the database 196 for all of the transactions sent from the service provider computer 106 to the third-party switch provider computer 112 in order to determine a percentage of transmission successes rather than or in addition to the number of transmission successes over the pre-set time period.

In step 386, an inquiry is conducted to determine if the transmission successes to the third-party switch provider computer 112 satisfy the operating threshold. In one example embodiment, the determination can be made by the service provider network monitoring module 194 or another portion of the service provider computer 106. For example, the service provider network monitoring module may obtain the configurable operating threshold from the database 196 or other memory and can compare that to the number and/or percentage of transmission successes identified in step 384. In one example, if responses are received from the third-party switch provider computer 112 within 5-15 seconds of a healthcare claim transaction that is exclusively received from a third-party switch provider computer 112, the operating threshold may be considered to have been met. In another example embodiment, if responses to a series of healthcare transactions being sent to the third-party switch provider computer 112 are received in less than 5 seconds and the timeouts for a series of healthcare claim transactions sent to the third-party switch provider computer 112 are below a level of about 20 percent of the healthcare claim transactions being sent to the third-party switch provider computer 112 by the service provider computer 106, the operating threshold may be considered to have been met. In another example embodiment, if notification is received by the service provider computer 106 from the third-party switch provider computer 112 that connectivity is restored, the operating threshold may be considered to have been met. In yet another example embodiment, if the network monitoring module 194 or another portion of the service provider computer 106 is not able to determine if the third-party switch provider computer 112 has restored connectivity for a predetermined amount of time, the operating threshold may be considered to have been met. In one example, the predetermined amount of time is between 1-1000 minutes. If the number and/or percentage of transmission successes does not satisfy (e.g., is less than or less than or equal to the operating threshold) operating threshold, the NO branch can be followed to FIG. 4 for the processing of additional healthcare transactions from pharmacy computers 104. If the number and/or percentage of transmission successes satisfies (e.g., is greater than or is greater than or equal to the operating threshold) the operating threshold, then the YES branch can be followed to step 386, where the service provider network monitoring module 194 or another portion of the service provider computer 106 can designate or otherwise determine that the third-party switch provider computer 112 is operating (e.g., receiving and processing healthcare transactions at a normal rate). This designation, like the designation that the third-party switch provider computer 112 is not operating, can be stored in the database 196 or other memory for access by the service provider network monitoring module 194 or another portion of the service provider computer 106. The process can then proceed to step 302 for the preparation and receipt of additional healthcare transactions from the one or more pharmacy computers 104 for multiple pharmacies.

Figure 4A:
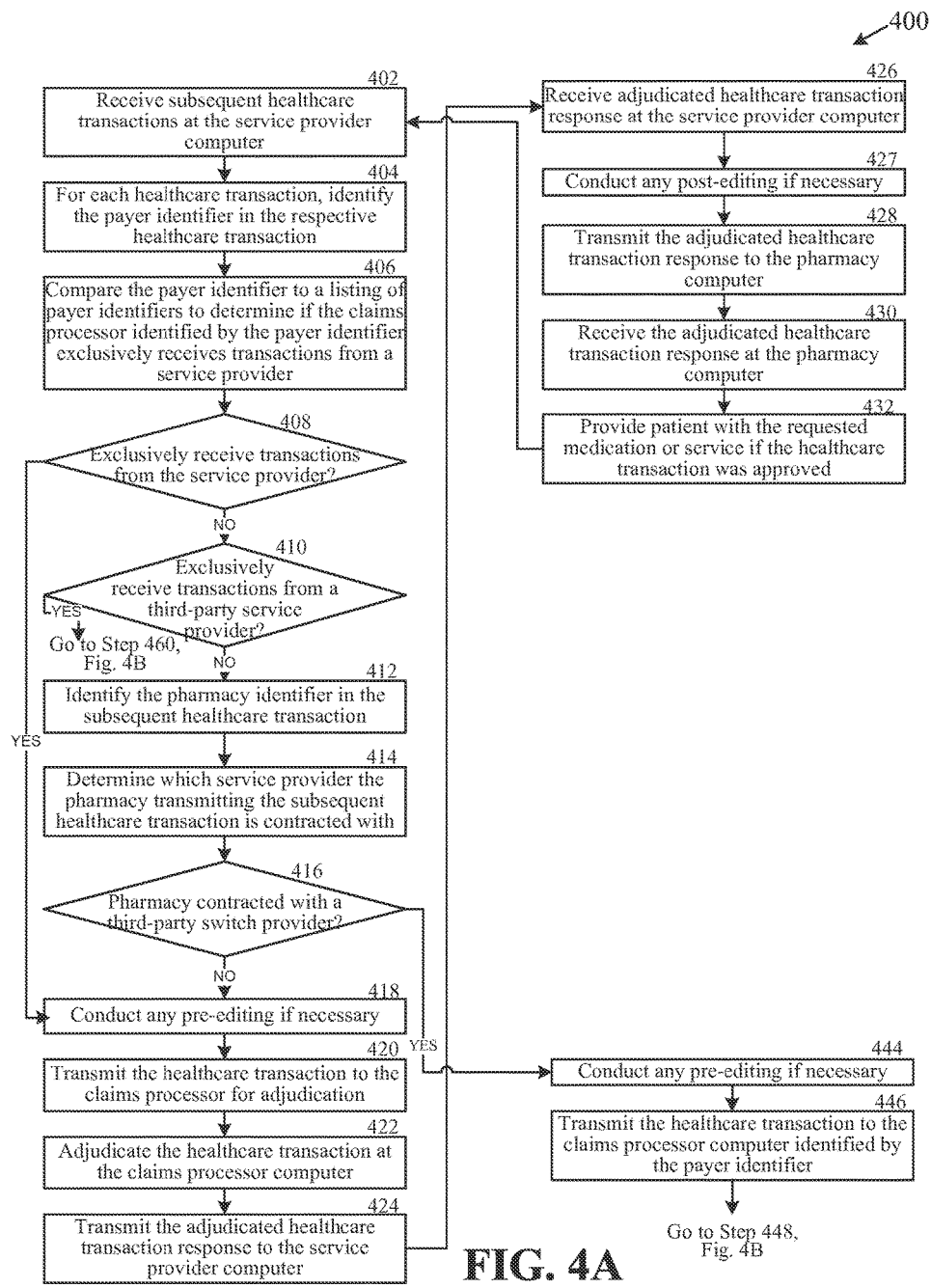
FIGS. 4A and 4B are a flow chart of an example method for determining if a third-party switch provider system is once again operating or otherwise processing electronically submitted healthcare transactions as part of the processing of electronically submitted healthcare transactions processed through a service provider computer, according to one exemplary embodiment of the disclosure.
Figure 4B:
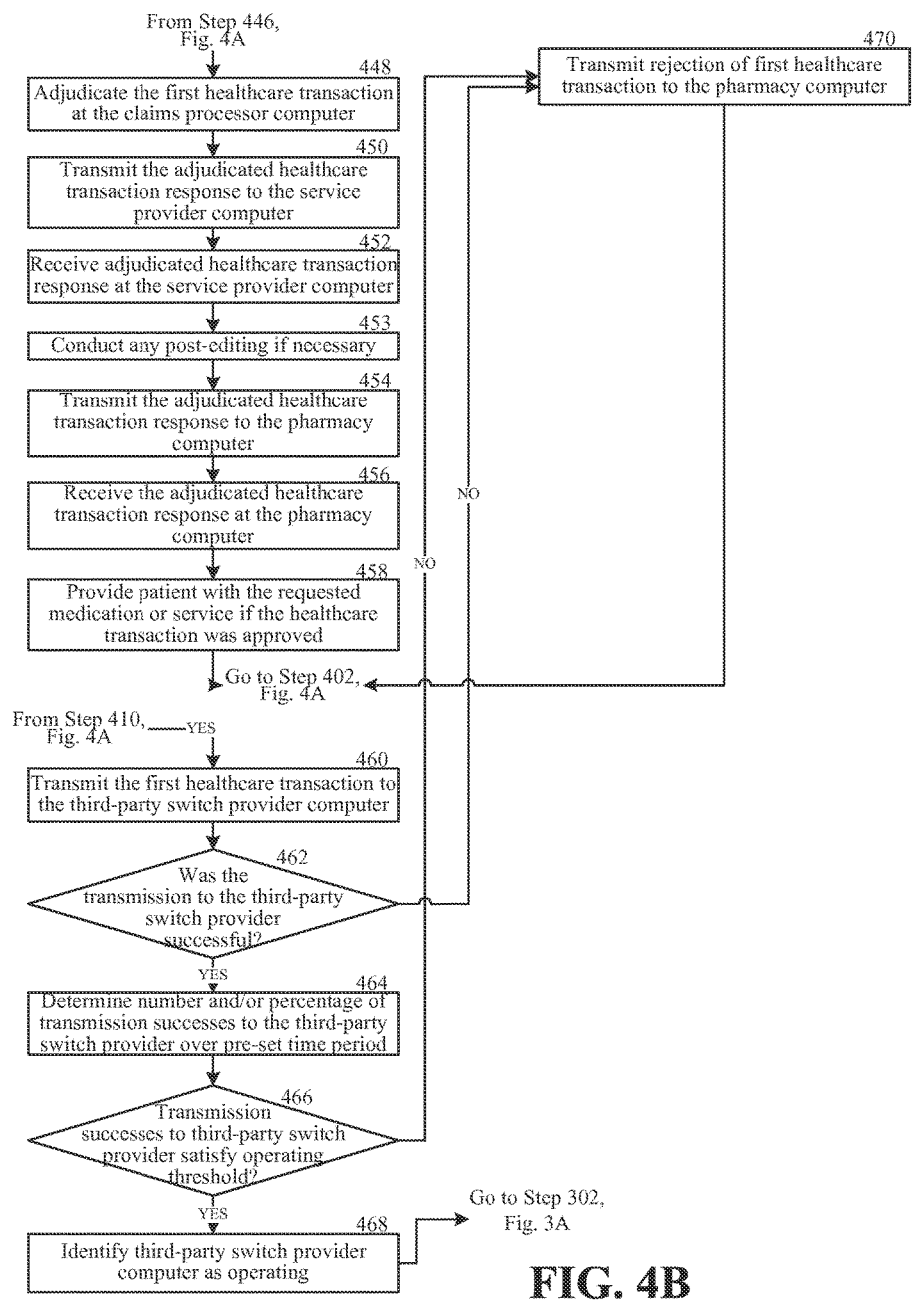

FIGS. 4A-B are a flow chart of an example method 400 for determining if a third-party switch provider system 112 is once again operating or otherwise processing electronically submitted healthcare transactions as part of the processing of electronically submitted healthcare transactions processed through a service provider computer 106, according to one exemplary embodiment of the disclosure. The exemplary method 400, described below, may be performed by a suitable service provider computer 106 and/or service provider network monitoring module 194. Referring now to FIGS. 1, 2, 3A-B, and 4A-B, the exemplary method 400 begins at step 402, where the service provider computer 106 receives subsequent healthcare claim transactions 208. The subsequent healthcare claim transactions 208 can number in the millions in certain example embodiments depending on the time frame. For example, each of the subsequent healthcare claim transactions 208 can be electronically transmitted by the healthcare provider computer 104 to the service provider computer 106 through the network 110. In step 404, the service provider computer 106 and/or the service provider network monitoring module 194 can determine the payer identifier in each of the subsequent healthcare claim transactions 208. For example, the payer identifier can be the BIN Number, BIN Number and PCN, or the BIN Number and Group ID provided in the healthcare claim transaction 208. The service provider network monitoring module 194 or another portion of the service provider computer 106 can parse each of the subsequent healthcare claim transactions 208 to identify the fields of the transaction 208 that include this information.

In step 406, the service provider network monitoring module 194 or another portion of the service provider computer 106 can compare the payer identifier from each of the subsequent transactions 208 to a listing of payer identifiers to determine if the claims processor computer identified by the payer identifier exclusively receives healthcare transactions from one of the intermediaries/switch provider/service providers. For example, the service provider network monitoring module 194 or another portion of the service provider computer 106 can compare the payer identifier to the listing to determine if a match exists, and based on that matching record, determine if the claims processor exclusively receives healthcare transactions from only one switch provider/service provider. In step 408, an inquiry is conducted to determine, based on the comparison in step 406, if the claims processor identified by the payer identifier exclusively receives healthcare transactions (such as the subsequent healthcare claim transaction 208 currently being evaluated) from the service provider computer 106. In one example, the determination is made by the service provider network monitoring module 194 or another portion of the service provider computer 106. If there is no exclusive arrangement between the claims processor identified by the payer identifier and the service provider computer 106, the NO branch is followed to step 410. Otherwise, the YES branch is followed to step 418.

In step 418, the service provider computer 106 conducts any pre-editing, if necessary, on each of the subsequent healthcare claim transactions 208 that are to be exclusively received by the service provider computer 106. The pre-edits may include verifying, adding, and/or editing information included in the particular subsequent healthcare claim transaction 208 prior to it being communicated to a claims processor computer 108. The service provider computer 106 electronically transmits the particular subsequent healthcare claim transaction 208 to the claims processor computer 108 in step 420. For example, the particular subsequent healthcare claim transaction 208 can be transmitted from the service provider computer 106 to the claims processor computer 108 via the network 110. The claims processor computer 108 receives and adjudicates the particular subsequent healthcare claim transaction 208 in step 422 to determine if the patient has coverage, to determine to what extent the patient's coverage covers the requested medication/product/service identified in the transaction 204, and to generate an adjudication 210 as to whether the particular transaction 208 is approved or rejected. Typically, if the particular transaction 208 is approved, the adjudicated response 210 provides the amount of the cost of the medication that will be covered by the claims processor/payer and the patient co-pay and if rejected, the adjudicated response 210 provides the reason for the rejection. In certain exemplary embodiments, the adjudication can be input into a field of the particular subsequent healthcare claim transaction 206 that is recognized by the service provider computer 106 and/or the healthcare provider computer 104. In step 424, the claims processor computer 108 electronically transmits the adjudicated subsequent healthcare claim transaction response 210 to the service provider computer 106 via, for example, the network 110.

The service provider computer 106 receives the adjudicated subsequent healthcare claim transaction response 210 from the claims processor computer 108 in step 426. In step 427, the service provider computer 106 and/or the network monitoring module 194 may conduct any post-editing to the adjudicated subsequent healthcare claim transaction response 210, if necessary, prior to sending the response 210 along to the pharmacy computer 104. In step 428, the service provider computer 106 electronically transmits the adjudicated subsequent healthcare claim transaction response 210 to the pharmacy computer 104. In one exemplary embodiment, the adjudicated response 210 is transmitted to the pharmacy computer 104 via the network 110. The adjudicated subsequent healthcare claim transaction response 210 is received at the pharmacy computer 104 in step 430. The pharmacist or other pharmacy employee may provide the patient with the medication requested in the particular subsequent healthcare claim transaction 208 upon receipt of any necessary patient co-pay or may explain the reasons for the transaction 208 being rejected during adjudication in step 432. The process then continues to step 402 for receipt and processing of additional healthcare transactions by the service provider computer 106.

Returning to step 410, an inquiry is conducted to determine, based on the comparison in step 406, if the claims processor identified by the payer identifier exclusively receives healthcare transactions (such as the particular subsequent healthcare claim transaction 208) from the third-party switch provider computer 112 or another intermediary computing system. In one example, the determination is made by the service provider network monitoring module 194 or another portion of the service provider computer 106. If there is no exclusive arrangement, the NO branch is followed to step 412. If there is an exclusive arrangement between the claims processor identified by the payer identifier and the third-party switch provider computer 112, the YES branch is followed to step 460.

In step 460, the service provider computer 106 electronically transmits the particular subsequent healthcare claim transaction 208 to the third-party switch provider computer 112. In one example, the transmission from the service provider computer 106 to the third-party switch provider computer 112 of the transaction 208 may be via the network 110. In step 462, an inquiry is conducted to determine if the transmission of the transaction 208 to the third-party switch provider computer 112 was successful. In one example embodiment, the determination may be made by the service provider network monitoring module 194 or another portion of the service provider computer 106. For example, the transmission would not be successful, if the transmission is rejected by the third-party switch provider computer 112, if there is no response from the third-party switch provider computer 112 to the service provider computer 106 regarding the transmission, or if the transmission times out (e.g., no response received from the third-party switch provider computer 112 by the service provider computer 106 within a predetermined time threshold of sending the transmission. In one example embodiment, the predetermined time threshold is configurable and in certain example embodiments is 15 seconds, however, any other time period between 0-300 seconds (including between 0-1000 milliseconds or any other fractions of a second(s) therein) is also possible. If the transmission to the third-party switch provider computer 112 was successful, the YES branch is followed to step 464. Otherwise, the NO branch is followed to step 470.

In an alternative example embodiment, in the inquiry of step 462, the transmission of the subsequent healthcare claim transaction 208 to the third-party switch provider computer 112 is not successful when the third-party switch provider computer 112 sends back a response to the service provider computer 106 indicating that the third-party switch provider computer 112 is not able to process the subsequent healthcare claim transaction 208 (e.g., the third-party switch provider computer 112 is down, experiencing an outage or partial outage or is otherwise not operating properly). The response may indicate that the third-party switch provider computer 112 is under an outage or partial outage or that failure of the third-party switch provider computer 112 is about to occur. In this alternative embodiment, if a response from the third-party switch provider computer 112 indicating a problem with the system 112 is not received by the service provider computer 106, the network monitoring module 194 or another portion of the service provider computer 106 will presume that the third-party switch provider computer 112 is once again operating properly. In this alternative embodiment, if a response is received indicating that the third-party switch provider computer 112 has a problem, the method may continue to step 470. If no response from the third-party switch provider computer 112 indicating a problem with the computer 112 is received by the service provider computer 106, the transmission of the subsequent healthcare claim transaction 208 is presumed to have been successful and steps 464-466 may be skipped and the method may continue to step 468.

In step 464, the service provider network monitoring module 194 or another portion of the service provider computer 106 can determine the number and/or percentage of transmission successes to the third-party switch provider computer 112 over a pre-set time period. Similar to that described in step 346, with reference to determining the number of transmission failures, the number of transmission successes to the third-party switch provider computer 112 can be similarly determined. In one example, embodiment, the pre-set time period is configurable based on the needs of the system administrator. In one example, the pre-set time period can be 5 minutes, however, any other time period between 0-120 minutes is contemplated within the scope of the disclosure. In one example embodiment, each time a transmission to the third-party switch provider computer 112 is successful, the service provider network monitoring module 194 or another portion of the service provider computer 106 can increment a counter variable in the database 196 or other memory. The successful transmission counter may be further associated with a timer to keep count of a number of successful transmissions to the third-party switch provider computer 112 over the pre-set time period. In addition, a counter variable may be maintained in the database 196 for all of the transactions sent from the service provider computer 106 to the third-party switch provider computer 112 in order to determine a percentage of transmission successes rather than or in addition to the number of transmission successes over the pre-set time period.

In step 466, an inquiry is conducted to determine if the transmission successes to the third-party switch provider computer 112 satisfy the operating threshold. In one example embodiment, the determination can be made by the service provider network monitoring module 194 or another portion of the service provider computer 106. For example, the service provider network monitoring module may obtain the configurable operating threshold from the database 196 or other memory and can compare that to the number and/or percentage of transmission successes identified in step 464. If the number and/or percentage of transmission successes does not satisfy (e.g., is less than or less than or equal to the operating threshold) operating threshold, the NO branch can be followed to step 470, where the service provider computer 106 electronically transmits the rejection of the particular subsequent healthcare transaction 212 to the pharmacy computer 104 via, for example, the network 110. The process then proceeds to step 402 for the receipt of subsequent healthcare transactions from the one or more pharmacy computers 104.

If the number and/or percentage of transmission successes satisfies (e.g., is greater than or is greater than or equal to the operating threshold) the operating threshold, then the YES branch can be followed to step 468, where the service provider network monitoring module 194 or another portion of the service provider computer 106 can designate or otherwise determine that the third-party switch provider computer 112 is operating (e.g., receiving and processing healthcare transactions at a normal rate). This designation, like the designation that the third-party switch provider computer 112 is not operating, can be stored in the database 196 or other memory for access by the service provider network monitoring module 194 or another portion of the service provider computer 106. The process can then proceed to step 302 for the preparation and receipt of additional healthcare transactions from the one or more pharmacy computers 104 for multiple pharmacies.

Returning to step 410, when the determination is that the payer identifier does not identify a claims processor computer 108 that exclusively receives transactions from the third-party switch provider computer 112, the NO branch is followed to step 412. In step 412, the service provider network monitoring module 194 or another portion of the service provider computer 106 identifies the pharmacy identifier in the particular subsequent healthcare claim transaction 208. In one example, the pharmacy identifier can be the NPI code, pharmacy name of pharmacy number within a pharmacy chain. In step 414, the service provider network monitoring module 194 or another portion of the service provider computer 106 can determine which intermediary switch/service provider (e.g., one of the service provider computer 106 or the third-party switch provider computer 112) the pharmacy identified by the pharmacy identifier in the particular subsequent healthcare claim transaction 208 is contracted with to receive healthcare transactions and pass those healthcare transactions on to the proper claims processor computer. For example, the service provider network monitoring module 194 or another portion of the service provider computer 106 may compare the pharmacy identifier from the particular transaction 208 to a table, listing, or schedule of pharmacy identifiers to identify a matching pharmacy identifier in a record, such as in the database 196. Based on the matching record (e.g., record states which intermediary is contracted with or records are organized by which intermediary the pharmacies are contracted with), the service provider network monitoring module 194 or another portion of the service provider computer 106 can determine which intermediary switch/service provider the pharmacy is contracted with.

In step 416, an inquiry is conducted to determine if the pharmacy identified by the pharmacy identifier in the particular subsequent healthcare claim transaction 208 is contracted with the third-party switch provider computer 112. As discussed above, the determination may be made by the service provider network monitoring module 194 or another portion of the service provider computer 106. If the identified pharmacy is contracted with the service provider computer 106, the NO branch is followed to step 418 for processing as discussed above. Otherwise, the YES branch is followed to step 444. As the third-party switch provider computer 112 is currently designated as being down or otherwise not processing healthcare transactions, those claims processors that are not exclusively served by the third-party switch provider computer 112 will receive transactions from the service provider computer 106, even if the pharmacy identified in the transaction is contracted with the third-party service provider. In one example embodiment, as the system is already designated down, the this group of transactions (claims processor/payer not exclusively served by the third-party switch provider 112 and the pharmacy identified in the transaction is contracted to receive intermediary switch/service provider services for healthcare transactions from the third-party switch provider computer 112) will not be sent initially to the third-party switch provider computer 112 until it is subsequently determined to be operating. Alternatively, the transaction 208 could still be initially transmitted to the third-party switch provider computer 112 and then, when the transmission fails, it could be redirected as discussed below by the service provider computer 106.

In step 444, due to the fact that the third-party switch provider 112 is not operating, the service provider computer 106 begins operating as the intermediary switch/service provider for the pharmacies contracted with the third-party switch provider computer 112 while it 112 is not operating so that those pharmacies will still be able to have their healthcare transactions adjudicated in a real-time or near real-time manner. As such, the service provider computer 106 conducts any pre-editing, if necessary, on the particular subsequent healthcare claim transaction 208. The pre-edits may include verifying, adding, and/or editing information included in the particular subsequent healthcare claim transaction 208 prior to it being communicated to a claims processor computer 108. The service provider computer 106 electronically transmits the particular subsequent healthcare claim transaction 208 to the claims processor computer 108 identified by the payer identifier in the transaction 208 in step 446. For example, the service provider network monitoring module 194 or another portion of the service provider computer 106 identifies the payer identifier in the transaction 204 and determines the claims processor computer to transmit the transaction 208 based on the payer identifier. The particular subsequent healthcare claim transaction 208 can then be transmitted from the service provider computer 106 to the claims processor computer 108 via the network 110. The claims processor computer 108 receives and adjudicates the first healthcare claim transaction 204 in step 448 to determine if the patient has coverage, to determine to what extent the patient's coverage covers the requested medication/product/service identified in the transaction 204, and to generate an adjudication 210 as to whether the transaction 208 is approved or rejected. In certain example embodiments, the adjudication can be input into a field of the particular subsequent healthcare claim transaction 208 that is recognized by the service provider computer 106 and/or the healthcare provider computer 104. In step 450, the claims processor computer 108 electronically transmits the adjudicated subsequent healthcare claim transaction response 210 to the service provider computer 106 via, for example, the network 110.

The service provider computer 106 receives the adjudicated subsequent healthcare claim transaction response 210 from the claims processor computer 108 in step 452. In step 453, the service provider computer 106 and/or the network monitoring module 194 may conduct any post-editing to the adjudicated subsequent healthcare claim transaction response 210, if necessary, prior to sending the response 210 along to the pharmacy computer 104. In step 454, the service provider computer 106 electronically transmits the adjudicated subsequent healthcare claim transaction response 210 to the pharmacy computer 104. In one exemplary embodiment, the adjudicated response 210 is transmitted to the pharmacy computer 104 via the network 110. The adjudicated subsequent healthcare claim transaction response 210 is received at the pharmacy computer 104 in step 456. The pharmacist or other pharmacy employee may provide the patient with the medication requested in the particular subsequent healthcare claim transaction 208 upon receipt of any necessary patient co-pay or may explain the reasons for the transaction 208 being rejected during adjudication in step 458. The process may then continue to step 402 for receipt and processing of additional healthcare transactions by the service provider computer 106.

The methods described and shown in FIGS. 2-4B may be carried out or performed in any suitable order as desired in various embodiments. Additionally, in certain exemplary embodiments, at least a portion of the operations may be carried out in parallel. Furthermore, in certain exemplary embodiments, less than or more than the operations described in FIGS. 2-4B may be performed. Likewise, while FIGS. 3A-4B have been described primarily in conjunction with FIG. 2 it will be appreciated that variations of FIG. 2 are available. In addition, in certain embodiments, the portions of the methods described in FIGS. 2-4B may be completed by different entities.

Accordingly, example embodiments disclosed herein can provide the technical effects of creating a system and methods that provide a real-time or near real time way to determine the operational status of third-party switch provider systems for receipt and processing of electronically submitted healthcare transactions from another intermediary, such as a service provider computer, and bypassing that third-party switch provider system when the other intermediary service provider computer system determines that the third-party switch provider computer system is not operating, as part of the processing of healthcare transactions. In this regard, pharmacies will be better able to have their healthcare transactions processed in real-time even when their contracted intermediary switch provider computer system is not operating, thereby allowing the pharmacy to continue receiving adjudications of its healthcare transactions and allowing the pharmacies to continue dispensing prescribed products and services to patients in a timely manner.

Further, example embodiments disclosed herein can provide the technical effects of creating a system and methods for continued monitoring and evaluation of the third-party switch provider system once it is determined to be not operating properly in order to determine when that third-party switch provider system is once again operating properly. Thus, pharmacies may continue to operate in a normal manner even when the intermediary switch provider system they contracted with for services is not able to provide those healthcare transaction processing services due to system downtime.

While certain example embodiments disclosed herein describe the service provider network monitoring module 194 as being separate from the service provider computer 106, in alternate embodiments, the service provider network monitoring module 194 or the functions that it completes may be part of the service provider computer 106. In those embodiments where the service provider network monitoring module 194 is incorporated into the service provider computer 106, and with regard to the methods described above, the blocks describing transmitting or receiving between the service provider computer 106 and the service provider network monitoring module 194 may be internal transmissions within the service provider computer 106 or may be omitted altogether. Further, while the exemplary embodiments described herein disclose certain actions occurring at the service provider computer 106 and/or the service provider network monitoring module 194, in alternative embodiments those actions described with reference to FIGS. 1-4B may alternately be completed at a pharmacy computer 104, and/or a combination of pharmacy computer 104 and the service provider computer 106. In those alternate embodiments, certain transmission/receiving actions described above with reference to FIGS. 1-4B may be omitted while others may be added, as understood by one or ordinary skill in the art. The intent being that in alternate embodiments, any of the devices/computers discussed in FIG. 1 are capable of completing any or any part of the methods described with reference to FIGS. 2-4B.

Various block and/or flow diagrams of systems and methods and/or computer program products according to example embodiments are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the disclosure may provide for a computer program product, that includes a computer usable medium (e.g., transitory or non-transitory) having a computer-readable program code or program instructions embodied therein, said computer-readable program code adapted to be executed to implement one or more functions specified in the flow diagram step or steps. The computer program instructions may also be loaded onto a computer or other programmable data processing apparatus to cause a series of operational elements or actions to be performed on the computer or other programmable apparatus to produce a computer-implemented process such that the instructions that execute on the computer or other programmable apparatus provide elements or steps for implementing the functions specified in the flow diagram blocks.

Accordingly, blocks of the block diagrams and flow diagrams support combinations of means for performing the specified functions, combinations of elements or actions for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of those set forth herein will be apparent having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A computer-implemented method, comprising:

receiving, by a service provider computer associated with a service provider and comprising one or more computer processors from a pharmacy computer for a pharmacy, a first healthcare transaction comprising a first patient identifier for a patient; a first medication identifier identifying a product or medication requested in the first healthcare transaction, a first pharmacy identifier identifying the pharmacy, and a first payer identifier;

identifying, by the service provider computer, at least one of the first payer identifier and the first pharmacy identifier in the first healthcare transaction;

determining, by the service provider computer and based at least in part on at least one of the first payer identifier and the first pharmacy identifier, that the first healthcare transaction needs to be transmitted to a third-party switch provider computer for processing of the first healthcare transaction;

transmitting, by the service provider computer, the first healthcare transaction to the third-party switch provider computer for processing of the first healthcare transaction by the third-party switch provider computer;

determining, by the service provider computer, that the transmission of the first healthcare transaction to the third-party switch provider computer was not successful, wherein the determining that the transmission was not successful comprises a determination that the transmission of the first healthcare transaction to the third-party switch provider computer timed out prior to receiving an acknowledgement from the third-party switch provider computer;

incrementing, by the service provider computer and based on the determination that the transmission was not successful, a transmission failure variable for transmission failures of healthcare transactions to the third-party switch provider computer;

accepting, by the service provider computer, the transmission failure variable;

determining, by the service provider computer and based at least in part on the transmission failure variable, that the transmission failure variable for the third-party switch provider computer has violated a failure threshold variable;

determining, by the service provider computer and based on the transmission failure variable violating the failure threshold variable, that the third-party switch provider computer is not operating;

receiving, by the service provider computer from a second pharmacy computer for a second pharmacy, a second healthcare transaction, wherein the second healthcare transaction is received after the first healthcare transaction and wherein the second healthcare transaction comprises: a second patient identifier for a second patient; a second medication identifier identifying a product or medication requested in the second healthcare transaction, a second pharmacy identifier identifying the second pharmacy, and a second payer identifier;

determining, by the service provider computer and based at least in part on the second pharmacy identifier, that the second healthcare transaction needs to be transmitted to the third-party switch provider computer for processing of the second healthcare transaction; and transmitting, by the service provider computer and based at least in part on the determination that the third-party switch provider computer is not operating, the second healthcare transaction to a second claims processor computer identified by the second payer identifier for adjudication.

2. The computer-implemented method of claim 1, further comprising:

determining, by the service provider computer and based at least in part on the payer identifier, that the third-party switch provider computer does not have an exclusive healthcare transaction processing agreement with the claims processor computer identified by the first payer identifier; and retransmitting, by the service provider computer and based at least in part on the determination that the third-party switch provider computer is not operating and the third-party switch provider computer does not have an exclusive healthcare transaction processing agreement with a first claims processor computer identified by the first payer identifier, the first healthcare transaction to the first claims processor computer for adjudication.

3. The computer-implemented method of claim 1, wherein the transmission failure variable comprises at least one of a total number of transmission failures to the third-party switch provider computer over a pre-set time period or a percentage of transmission failures to the third-party switch provider computer over the pre-set time period.

4. The computer-implemented method of claim 1, further comprising:

receiving, by the service provider computer from a third pharmacy computer for a third pharmacy, a third healthcare transaction, wherein the third healthcare transaction is received after the first healthcare transaction and wherein the third healthcare transaction comprises: a third patient identifier for a third patient; a third medication identifier identifying a product or medication requested in the third healthcare transaction, a third pharmacy identifier identifying a pharmacy transmitting the third healthcare transaction, and a third payer identifier;

determining, by the service provider computer and based at least in part on the third payer identifier, that the third-party switch provider computer does have an exclusive healthcare transaction processing agreement with a third claims processor computer identified by the third payer identifier;

transmitting, by the service provider computer and based at least in part on the determination that the third-party switch provider computer does have the exclusive healthcare transaction processing agreement with the third claims processor computer, the third healthcare transaction to the third-party switch provider computer, wherein the third-party switch provider computer is currently determined to be not operating;

determining, by the service provider computer and based at least in part on the transmission of the third healthcare transaction to the third-party switch provider computer, if the third-party switch provider computer is still not operating.

5. A computer-implemented method, comprising:

receiving, by a service provider computer associated with a service provider and comprising one or more computer processors from a first pharmacy computer for a first pharmacy, a first healthcare transaction comprising a first patient identifier for a patient; a first medication identifier identifying a product or medication requested in the first healthcare transaction, a first pharmacy identifier identifying the first pharmacy, and a first payer identifier;

identifying, by the service provider computer, at least one of the first payer identifier and the first pharmacy identifier in the first healthcare transaction;

determining, by the service provider computer and based at least in part on at least one of the first payer identifier and the first pharmacy identifier, that the first healthcare transaction needs to be transmitted to a third-party switch provider computer for processing of the first healthcare transaction;

transmitting, by the service provider computer, the first healthcare transaction to the third-party switch provider computer for processing;

determining, by the service provider computer, that the transmission of the first healthcare transaction to the third-party switch provider computer was not successful;

determining, by the service provider computer and based at least in part on a comparison of a transmission failure variable for the third-party switch provider computer to a failure threshold variable, that the transmission failure variable for the third-party switch provider computer violates the failure threshold variable;

designating, by the service provider computer and based on the transmission failure variable violating the failure threshold variable, the third-party switch provider computer as not operating;

receiving, by the service provider computer from a second pharmacy computer for a second pharmacy, a second healthcare transaction, wherein the second healthcare transaction is received after the first healthcare transaction and wherein the second healthcare transaction comprises: a second patient identifier for a second patient; a second pharmacy identifier identifying a pharmacy transmitting the second healthcare transaction, and a second payer identifier;

determining, by the service provider computer and based at least in part on the second pharmacy identifier, that the second healthcare transaction needs to be transmitted to the third-party switch provider computer for processing of the second healthcare transaction; and transmitting, by the service provider computer and based at least in part on the determination that the third-party switch provider computer is not operating, the second healthcare transaction to a second claims processor computer identified by the second payer identifier for adjudication.

6. The computer-implemented method of claim 5, further comprising:

determining, by the service provider computer and based on the first payer identifier, that the third-party switch provider computer does have an exclusive healthcare transaction processing agreement with a first claims processor computer identified by the first payer identifier;

generating, by the service provider computer and based on the determination that the transmission of the first healthcare transaction to the third-party switch provider computer was not successful, a rejection of the first healthcare transaction; and transmitting, by the service provider computer, the rejection of the first healthcare transaction to the first pharmacy computer.

7. The computer-implemented method of claim 5, wherein determining that the transmission of the first healthcare transaction to the third-party switch provider computer was not successful comprises at least one of:

a determination that the transmission of the first healthcare transaction to the third-party switch provider computer timed out prior to receiving an acknowledgement from the third-party switch provider computer;

a determination that the third-party switch provider computer was non-responsive to the transmission of the first healthcare transaction by the service provider computer; and a determination that the third-party switch provider computer rejected receipt of the transmission of the first healthcare transaction by the service provider computer.

8. The computer-implemented method of claim 5, further comprising:

incrementing, by the service provider computer and based on the determination that the transmission was not successful, a transmission failure variable for transmission failures of healthcare transactions to the third-party switch provider computer; and accepting, by the service provider computer, the transmission failure variable from a data storage device.

9. The computer-implemented method of claim 5, further comprising:

comparing the first payer identifier to a listing of payer identifiers identifying claims processor computers that have exclusive healthcare transaction processing agreements with the third-party switch provider computer to determine if a match exists;

determining, by the service provider computer and based at least in part on the determination that a match does not exist, that the third-party switch provider computer does not have an exclusive healthcare transaction processing agreement with a first claims processor computer identified by the first payer identifier; and retransmitting, by the service provider computer and based at least in part on the determination that the third-party switch provider computer is not operating and the third-party switch provider computer does not have an exclusive healthcare transaction processing agreement with the first claims processor computer identified by the first payer identifier, the first healthcare transaction to the first claims processor computer for adjudication.

10. The computer-implemented method of claim 5, further comprising:

receiving, by the service provider computer from a third pharmacy computer for a third pharmacy, a third healthcare transaction, wherein the third healthcare transaction is received after the first healthcare transaction and wherein the third healthcare transaction comprises: a third patient identifier for a third patient; a third pharmacy identifier identifying a pharmacy transmitting the third healthcare transaction, and a third payer identifier;

comparing, by the service provider computer, the third payer identifier to a listing of payer identifiers identifying claims processor computers that have exclusive healthcare transaction processing agreements with the third-party switch provider computer to determine if a match exists;

determining, by the service provider computer and based at least in part on the determination that a match exists, that the third-party switch provider computer does have an exclusive healthcare transaction processing agreement with a third claims processor computer identified by the third payer identifier;

transmitting, by the service provider computer and based at least in part on the determination that the third-party switch provider computer does have the exclusive healthcare transaction processing agreement with the third claims processor computer, the third healthcare transaction to the third-party switch provider computer, wherein the third-party switch provider computer is currently determined to be not operating; and determining, by the service provider computer and based at least in part on the transmission of the third healthcare transaction to the third-party switch provider computer, if the third-party switch provider computer is still not operating.

11. The computer-implemented method of claim 10, wherein determining if the third-party switch provider computer is still not operating comprises:

determining, by the service provider computer, if the transmission of the third healthcare transaction to the third-party switch provider computer was successful;

incrementing, by the service provider computer and based at least in part on a positive determination that the transmission of the third healthcare transaction was successful, a transmission success variable for the third-party switch provider;

comparing, by the service provider computer, the transmission success variable to an operating threshold variable to determine if the transmission success variable satisfies the operating threshold variable; and designating, by the service provider computer and based at least in part on the determination that the transmission success variable satisfies the operating threshold variable, that the third-party switch provider computer as operating.

12. The computer-implemented method of claim 5, wherein the transmission failure variable comprises at least one of a total number of transmission failures to the third-party switch provider computer over a pre-set time period or a percentage of transmission failures to the third-party switch provider computer over the pre-set time period.

13. A system, comprising:

at least one memory operable to store computer-executable instructions; and at least one processor configured to access the at least one memory and execute the computer-executable instructions to:

receive, from a first pharmacy computer for a first pharmacy, a first healthcare transaction comprising a first patient identifier for a patient; a first medication identifier identifying a product or medication requested in the first healthcare transaction, a first pharmacy identifier identifying the first pharmacy, and a first payer identifier;

identify at least one of the first payer identifier and the first pharmacy identifier in the first healthcare transaction;

determine, based at least in part on at least one of the first payer identifier and the first pharmacy identifier, that the first healthcare transaction needs to be transmitted to a third-party switch provider computer for processing of the first healthcare transaction;

direct communication of the first healthcare transaction to the third-party switch provider computer for processing;

determine that the transmission of the first healthcare transaction to the third-party switch provider computer was not successful;

determine, based at least in part on a comparison of a transmission failure variable for the third-party switch provider computer to a failure threshold variable, that the transmission failure variable for the third-party switch provider computer violates the failure threshold variable;

designate, based on the transmission failure variable violating the failure threshold variable, the third-party switch provider computer as not operating;

receive, from a second pharmacy computer for a second pharmacy, a second healthcare transaction, wherein the second healthcare transaction is received after the first healthcare transaction and wherein the second healthcare transaction comprises: a second patient identifier for a second patient; a second pharmacy identifier identifying a pharmacy transmitting the second healthcare transaction, and a second payer identifier;

determine, based at least in part on the second pharmacy identifier, that the second healthcare transaction needs to be transmitted to the third-party switch provider computer for processing of the second healthcare transaction; and direct, based at least in part on the determination that the third-party switch provider computer is not operating, communication of the second healthcare transaction to a second claims processor computer identified by the second payer identifier for adjudication.

14. The system of claim 13, wherein the processor is further configured to access the at least one memory and execute the computer-executable instructions to:

determine, based on the first payer identifier, that the third-party switch provider computer does have an exclusive healthcare transaction processing agreement with a first claims processor computer identified by the first payer identifier;

generate, based on the determination that the transmission of the first healthcare transaction to the third-party switch provider computer was not successful, a rejection of the first healthcare transaction; and direct communication of the rejection of the first healthcare transaction to the first pharmacy computer.

15. The system of claim 13, wherein to determine that the transmission of the first healthcare transaction to the third-party switch provider computer was not successful comprises at least one of:

a determination that the transmission of the first healthcare transaction to the third-party switch provider computer timed out prior to receiving an acknowledgement from the third-party switch provider computer;

a determination that the third-party switch provider computer was non-responsive to the transmission of the first healthcare transaction by the service provider computer; and a determination that the third-party switch provider computer rejected receipt of the transmission of the first healthcare transaction by the service provider computer.

16. The system of claim 13, wherein the processor is further configured to access the at least one memory and execute the computer-executable instructions to:

increment, based on the determination that the transmission was not successful, a transmission failure variable for transmission failures of healthcare transactions to the third-party switch provider computer; and accept the transmission failure variable from a data storage device.

17. The system of claim 13, wherein the processor is further configured to access the at least one memory and execute the computer-executable instructions to:
compare the first payer identifier to a listing of payer identifiers identifying claims processor computers that have exclusive healthcare transaction processing agreements with the third-party switch provider computer to determine if a match exists;
determine, based at least in part on the determination that a match does not exist, that the third-party switch provider computer does not have an exclusive healthcare transaction processing agreement with a first claims processor computer identified by the first payer identifier; and
redirecting, based at least in part on the determination that the third-party switch provider computer is not operating and the third-party switch provider computer does not have an exclusive healthcare transaction processing agreement with the first claims processor computer identified by the first payer identifier, communication of the first healthcare transaction to the first claims processor computer for adjudication.

18. The system of claim 13, wherein the processor is further configured to access the at least one memory and execute the computer-executable instructions to:
receive, from a third pharmacy computer for a third pharmacy, a third healthcare transaction, wherein the third healthcare transaction is received after the first healthcare transaction and wherein the third healthcare transaction comprises: a third patient identifier for a third patient; a third pharmacy identifier identifying a pharmacy transmitting the third healthcare transaction, and a third payer identifier;
compare the third payer identifier to a listing of payer identifiers identifying claims processor computers that have exclusive healthcare transaction processing agreements with the third-party switch provider computer to determine if a match exists;
determine, based at least in part on the determination that a match exists, that the third-party switch provider computer does have an exclusive healthcare transaction processing agreement with a third claims processor computer identified by the third payer identifier;
direct, based at least in part on the determination that the third-party switch provider computer does have the exclusive healthcare transaction processing agreement with the third claims processor computer, communication of the third healthcare transaction to the third-party switch provider computer, wherein the third-party switch provider computer is currently determined to be not operating; and
determine, based at least in part on the transmission of the third healthcare transaction to the third-party switch provider computer, if the third-party switch provider computer is still not operating.

19. The system of claim 18, wherein the processor is further configured to determine if the third-party switch provider computer is still not operating by accessing the at least one memory and executing the computer-executable instructions to:
determine if the transmission of the third healthcare transaction to the third-party switch provider computer was successful;
increment, based at least in part on a positive determination that the transmission of the third healthcare transaction was successful, a transmission success variable for the third-party switch provider;
compare the transmission success variable to an operating threshold variable to determine if the transmission success variable satisfies the operating threshold variable; and
designate, based at least in part on the determination that the transmission success variable satisfies the operating threshold variable, that the third-party switch provider computer as operating.

20. A computer-implemented method, comprising:
receiving, by a service provider computer associated with a service provider and comprising one or more computer processors from a first pharmacy computer for a first pharmacy, a first healthcare transaction comprising a first patient identifier for a patient; a first medication identifier identifying a product or medication requested in the first healthcare transaction, a first pharmacy identifier identifying the first pharmacy, and a first payer identifier;
identifying, by the service provider computer, at least one of the first payer identifier and the first pharmacy identifier in the first healthcare transaction;
determining, by the service provider computer and based at least in part on at least one of the first payer identifier and the first pharmacy identifier, that the first healthcare transaction needs to be transmitted to a third-party switch provider computer for processing of the first healthcare transaction;
transmitting, by the service provider computer, the first healthcare transaction to the third-party switch provider computer for processing:
receiving, by the service provider computer and from the third-party switch provider computer, a response indicating that the third-party switch provider computer is not able to process the first healthcare transaction;
designating, by the service provider computer and based on the response from the third-party switch provider computer, the third-party switch provider computer as not operating;
receiving, by the service provider computer from a second pharmacy computer for a second pharmacy, a second healthcare transaction, wherein the second healthcare transaction is received after the first healthcare transaction and wherein the second healthcare transaction comprises: a second patient identifier for a second patient; a second pharmacy identifier identifying a pharmacy transmitting the second healthcare transaction, and a second payer identifier;
determining, by the service provider computer and based at least in part on the second pharmacy identifier, that the second healthcare transaction needs to be transmitted to the third-party switch provider computer for processing of the second healthcare transaction; and
transmitting, by the service provider computer and based at least in part on the determination that the third-party switch provider computer is not operating, the second healthcare transaction to a second claims processor computer identified by the second payer identifier for adjudication.

* * * * *